United States Patent
Puri et al.

(10) Patent No.: US 6,518,061 B1
(45) Date of Patent: Feb. 11, 2003

(54) IL-13 RECEPTOR SPECIFIC CHIMERIC PROTEINS AND USES THEREOF

(75) Inventors: Raj K. Puri, North Potomac, MD (US); Waldemar Debinski, Hummelstown, PA (US); Ira Pastan, Potomac, MD (US); Nicholas Obiri, N. Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/913,370

(22) PCT Filed: Mar. 15, 1996

(86) PCT No.: PCT/US96/03486

§ 371 (c)(1),
(2), (4) Date: Feb. 17, 1998

(87) PCT Pub. No.: WO96/29417

PCT Pub. Date: Sep. 26, 1996

Related U.S. Application Data

(63) Continuation-in-part of application No. 08/404,685, filed on Mar. 15, 1995, now Pat. No. 5,614,191.

(51) Int. Cl.[7] .......................... C12N 15/74; C12N 5/10; C12P 21/04
(52) U.S. Cl. ................... 435/320.1; 435/69.7; 435/328; 435/334; 530/351
(58) Field of Search .......................... 424/143.1, 155.1, 424/174.1; 435/69.7, 91.1, 328, 334, 320.1; 530/387.7, 387.3, 388.22, 351; 514/12; 536/23.4, 235, 23.53

(56) References Cited

U.S. PATENT DOCUMENTS

| | | |
|---|---|---|
| 5,082,927 A | 1/1992 | Pastan et al. |
| 5,596,072 A | 1/1997 | Culpepper et al. |
| 5,614,191 A | 3/1997 | Puri et al. |
| 5,919,456 A | 7/1999 | Puri, et al. ............... 424/181.1 |

FOREIGN PATENT DOCUMENTS

| | | |
|---|---|---|
| WO | WO 94/04680 | 3/1994 |

OTHER PUBLICATIONS

Chaudhary et al, *Nature*, 335:369–372 (1988).
Chester et al., *Tibtec* 13; vol. 13, 294–300 (1995).
Debinski et al., *J. Biol. Chem.*, vol. 268,19:14065 (1993).
Debinski et al., *Bioconjugate Chem*, vol. 5, 40–46 (1994).
Gottstein, et al., *Annab of Oncology*, vol. 5 Supplement 1 S97–103 (1994).
McKenzie et al. *Proc. Natl. Acad. Sci. USA*, 90:3735 (1993).
Obiri et al., *J. Biol. Chem.*, vol. 270, 15:8797 (1995).
Pastan et al., *Ann. Rev. Biochem.*, 61:331–354 (1992).
Paul, *Fundamental Immunology*, Third Edition, 784–789 (1993).
Puri et al., *Blood*, vol. 87 No. 10, 4333–4339 (1996).
Minty et al., *Nature*, 362:248 (1993).
Thrush, et al., *Ann. Rev. Immunol.*, vol. 14, 49–71 (1996).
Vita et al., *Journ. of Biol. Chem.*, 270:3512 (1995).
*EMBO Journal*, vol. 12, No. 7, 1993, Eynsham, GB, pp. 2663–2670, XP002011860, S.M. Zurawski et al., "Receptors for Interleukin–13 and Interleukin–4 are complex and share a novel component that functions in signal transduction".
*Journal of Biological Chemistry*, vol. 270, No. 28, Jul. 14, 1995, MD US, pp. 16775–16780, XP002011861, W. Debinski, et al.: "A novel chimeric protein composed of Interleukin–13 and Pseudomonas Exotoxin is highly cytotoxic to human carcinoma cells expressing receptors for Interleukin–13 and Interleukin–4".
Robert J. Kreitman, et al., "A Circularly Permuted Recombinant Interleukin 4 Toxin with Increased Activity," *Proc. Natl. Acad. Sci.*, 91:6889–6893 (Jul. 1994).
Robert J. Kreitman, et al., "Increased Antitumor Activity of a Circularly Permuted Interleukin 4–Toxin in Mice with Interleukin 4 Receptor–bearing Human Carcinoma," *Cancer Research*, 55:3357–3363, Aug. 1, 1995.
Raj K. Puri, et al. "An Improved Circularly Permuted Interleukin 4–Toxin is Highly Cytotoxic to Human Renal Cell Carcinoma Cells," *Cellular Immunology*, 171:80–86 (1996).

*Primary Examiner*—Brenda Brumback
(74) *Attorney, Agent, or Firm*—Townsend and Townsend and Crew LLP

(57) ABSTRACT

The present invention provides a method and compositions for specifically delivering an effector molecule to a tumor cell bearing an IL-13 receptor. The method involves providing a chimeric molecule that comprises an effector molecule attached to a circularly permuted IL-13 ("cpIL-13") that specifically binds an IL-13 receptor and contacting the tumor cell with the chimeric molecule. The compositions include chimeric molecules comprising effector molecules such as modified Pseudomonas exotoxin attached to a cpIL-13. The invention further provides vectors encoding the chimeric molecules.

12 Claims, No Drawings

IL-13 RECEPTOR SPECIFIC CHIMERIC PROTEINS AND USES THEREOF

RELATED APPLICATIONS

This application is a 35 U.S.C. §371 national stage filing of international application PCT/US96/0348, filed Mar. 15, 1996, which is a continuation-in-part of U.S. application Ser. No. 08/404,685, filed Mar. 15, 1995, now U.S. Pat. No. 5,614,191. The contents of these applications are incorporated herein by reference for all purposes.

FIELD OF THE INVENTION

This invention relates to methods of specifically delivering an effector molecule to a tumor cell. In particular this invention relates to chimeric molecules that specifically bind to IL-13 receptors and their use to deliver molecules having a particular activity to tumors overexpressing IL-13 receptors.

BACKGROUND OF THE INVENTION

In a chimeric molecule, two or more molecules that exist separately in their native state are joined together to form a single molecule having the desired functionality of all of its constituent molecules. Frequently, one of the constituent molecules of a chimeric molecule is a "targeting molecule". The targeting molecule is a molecule such as a ligand or an antibody that specifically binds to its corresponding target, for example a receptor on a cell surface. Thus, for example, where the targeting molecule is an antibody, the chimeric molecule will specifically bind (target) cells and tissues bearing the epitope to which the antibody is directed.

Another constituent of the chimeric molecule may be an "effector molecule". The effector molecule refers to a molecule that is to be specifically transported to the target to which the chimeric molecule is specifically directed. The effector molecule typically has a characteristic activity that is desired to be delivered to the target cell. Effector molecules include cytotoxins, labels, radionuclides, ligands, antibodies, drugs, liposomes, and the like.

In particular, where the effector component is a cytotoxin, the chimeric molecule may act as a potent cell-killing agent specifically targeting the cytotoxin to cells bearing a particular target molecule. For example, chimeric fusion proteins which include interleukin 4 (IL-4) or transforming growth factor (TGFα) fused to Pseudomonas exotoxin (PE) or interleukin 2 (IL-2) fused to Diphtheria toxin (DT) have been shown-to specifically target and kill cancer cells (Pastan et al., *Ann. Rev. Biochem.*, 61: 331–354 (1992)).

Generally, it is desirable to increase specificity and affinity and decrease cross-reactivity of chimeric cytotoxins in order to increase their efficacy. To the extent a chimeric molecule preferentially selects and binds to its target (e.g. a tumor cell) and not to a non-target (e.g. a healthy cell), side effects of the chimeric molecule will be minimized. Unfortunately, many targets to which chimeric cytotoxins have been directed (e.g. the IL-2 receptor), while showing elevated expression on tumor cells, are also expressed at significant levels on healthy cells. Thus, chimeric cytotoxins directed to these targets frequently show adverse side-effects as they bind non-target (e.g., healthy) cells that also express the targeted receptor.

SUMMARY OF THE INVENTION

The present invention provides methods and compositions for specifically delivering an effector molecule to a tumor cell. In particular, the present invention provides chimeric molecules that specifically target tumor cells with less binding to healthy cells than other analogous chimeric molecules known in the prior art.

The improved specific targeting of this invention is premised, in part, on the discovery that tumor cells, especially carcinomas such as renal cell carcinoma, overexpress IL-13 receptors at extremely high levels. The extremely high level of IL-13 receptor expression on target tumor cells permits the use of lower dosages of chimeric molecule to deliver the same amount of effector molecule to the target cells and also results in reduced binding of non-tumor cells.

In a preferred embodiment, this invention provides for a method for specifically delivering an effector molecule to a tumor cell bearing an IL-13 receptor. The method involves providing a chimeric molecule comprising an effector molecule attached to a targeting molecule that specifically binds to an IL-13 receptor and contacting the tumor with the chimeric molecule resulting in binding of the chimeric molecule to the tumor cell.

The targeting molecule is preferably either a ligand, such as IL-13 or circularly permuted IL-13 (cpIL-13, especially cpIL-13 where the native IL-13 is opened between residues 43 and 44 (Gly and Met respectively) to produce a cpIL-13 having Met44 as the amino terminus and Gly43 as its carboxyl terminus) that specifically binds an IL-13 receptor, or an anti-IL-13 receptor antibody. The targeting molecule may be conjugated to the effector molecule, or where both targeting and effector molecules are polypeptides, the targeting molecule may be joined to the effector molecule through one or more peptide bonds thereby forming a fusion protein. Suitable effector molecules include a cytotoxin, a label, a radionuclide, a drug, a liposome, a ligand, and an antibody. In a particularly preferred embodiment, the effector is a cytotoxin, more specifically a Pseudomonas exotoxin such as PE38QQR or PE4E. Where the Pseudomonas exotoxin is fused to an IL-13 targeting molecule, preferred fusion proteins include, but are not limited to IL-13-PE38QQR, IL-13-PE4E, cpIL-13-PE38QQR, and cpIL-13-PE4E.

In another embodiment, this invention provides a method for impairing the growth of tumor cells, more preferably solid tumor cells, bearing an IL-13 receptor. The method involves contacting the tumor with a chimeric molecule comprising an effector molecule selected from the group consisting of a cytotoxin, a radionuclide, a ligand and an antibody. The effector molecule is attached to a targeting molecule that specifically binds a human IL-13 receptor. The targeting molecule is preferably a ligand (such as IL-13) that binds the IL-13 receptor or an anti-IL-13 receptor antibody. Preferred cytotoxic effector molecules include Pseudomonas exotoxin, Diphtheria toxin, ricin and abrin. Psuedomonas exotoxins, such as PE38QQR and PE4E, are particularly preferred. The targeting molecule may be conjugated or fused to the effector molecule with attachment by fusion preferred for cytotoxic effector molecules. The tumor growth that is impaired may be tumor growth in a human. Thus the method may further comprise administering the chimeric molecule to a human intravenously into a body cavity, or into a human or an organ.

In yet another embodiment, this invention provides for a method of detecting the presence or absence of a tumor. The method involves contacting the tumor with a chimeric molecule comprising a detectable label attached to a targeting molecule that specifically binds a human IL-13 receptor and detecting the presence or absence of the label. In a preferred embodiment, the label is selected from the group consisting of a radioactive label, an enzymatic label, an electron dense label, and a fluorescent label. Preferred targeting molecules include, but are not limited to IL-13, cpIL-13, and anti-IL-13R antibodies.

This invention also provides for vectors comprising a nucleic acid sequence encoding a chimeric polypeptide fusion protein comprising an IL-13, or a cpIL-13, attached to a second polypeptide. The chimeric polypeptide fusion protein specifically binds to a tumor cell bearing an IL-13 receptor. A preferred vector encodes an IL-13-PE or cpIL-13-PE fusion protein and more preferably encodes an IL-13-PE38QQR, IL-13-PE4E, cpIL-13-PE38QQR, or cpIL-13-PE4E fusion protein.

This invention also provides for host cells comprising a nucleic acid sequence encoding a chimeric polypeptide fusion protein comprising an IL-13 attached to a second polypeptide. A preferred host cell comprises a nucleic acid encoding an IL-13-PE, or cpIL-13-PE, fusion protein, more preferably encoding an IL-13-PE38QQR, IL-I3-PE4E, cpIL-13-PE38QQR, or cpIL-13-PE4E fusion protein. The encoded fusion protein specifically binds to a tumor cell bearing an IL-13 receptor. Particularly preferred host cells are bacterial host cells, especially *E. coli* cells.

In still yet another embodiment, this invention provides chimeric molecules that specifically bind a tumor cell bearing an IL-13 receptor. In one preferred embodiment, the chimeric molecule comprises a cytotoxic molecule attached to a targeting molecule that specifically binds an IL-13. The targeting molecule may be conjugated or fused to the cytotoxic molecule. In a preferred embodiment, the targeting molecule is fused to the cytotoxin thereby forming a single-chain fusion protein. Particularly preferred targeting molecules are IL-13, cpIL-13, or an antibody that specifically binds to the IL-13 receptor. Preferred cytotoxic molecules include Pseudomonas exotoxin, Diphthena toxin, ricin, and abrin, with Pseudomonas exotoxins (especially PE38QQR or PE4E) being most preferred.

In another preferred embodiment, the chimeric molecule comprises an effector molecule attached to an antibody that specifically binds to an IL-13 receptor. Effector molecules include a cytotoxin, a label, a radionuclide, a drug, liposome, a ligand and an antibody. The effector molecule may be fused or conjugated to the antibody.

The invention additionally provides for pharmacological compositions comprising a pharmaceutically acceptable carrier and a chimeric molecule where the chimeric molecule comprises and effector molecule attached to a targeting molecule that specifically binds to an IL-13 receptor. The targeting and effector molecules may be conjugated or fused to each other. Particularly preferred targeting molecules include IL-13, cpIL-13, and anti-IL-13 receptor antibodies, while preferred effector molecules include a cytotoxin, a label, a radionuclide, a drug, a liposome, a ligand and an antibody. A preferred pharmacological composition includes an IL-13-PE fusion protein, more preferably a IL-13-PE38QQR, IL-13-PE4E, cpIL-13-PE38QQR, or cpIL-13-PE4E fusion protein.

Definitions

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule. Specific delivery typically results in greater than 2 fold, preferably greater than 5 fold, more preferably greater than 10 fold and most preferably greater than 100 fold increase in amount of delivered molecule (per unit time) to a cell or tissue bearing the target molecule as compared to a cell or tissue lacking the target molecule or marker.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino acids.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

A "ligand", as used herein, refers generally to all molecules capable of reacting with or otherwise recognizing or binding to a receptor on a target cell. Specifically, examples of ligands include, but are not limited to, antibodies, lymphokines, cytokines, receptor proteins such as CD4 and CD8, solubilized receptor proteins such as soluble CD4, hormones, growth factors, and the like which specifically bind desired target cells.

The term "cpIL-13" is used to designate a circularly permuted (cp) IL-13. Circular permutation is functionally equivalent to taking a straight-chain molecule, fusing the ends (directly or through a linker) to form a circular molecule, and then cutting the circular molecule at a different location to form a new straight chain molecule with different termini.

DETAILED DESCRIPTION

I. Chimeric Molecules Targeted to the IL13 Receptor

The present invention provides a method for specifically delivering an effector molecule to a tumor cell. This method involves the use of chimeric molecules comprising a targeting molecule attached to an effector molecule. The chimeric molecules of this invention specifically target tumor cells while providing reduced binding to non-target cells as compared to other targeted chimeric molecules known in the art.

The improved specific targeting of this invention is premised, in part, on the discovery that solid tumors, especially carcinomas, overexpress IL-13 receptors at extremely high levels. While the IL-13 receptors (IL-13R) are overexpressed on tumor cells, expression on other cells (e.g. monocytes, B cells, and T cells) appears negligible. Thus, by specifically targeting the IL-13 receptor, the present invention provides chimeric molecules that are specifically directed to solid tumors while minimizing targeting of other cells or tissues.

In a preferred embodiment, this invention provides for compositions and methods for impairing the growth of tumors. The methods involve providing a chimeric molecule comprising a cytotoxic effector molecule attached to a targeting molecule that specifically binds an IL-13 receptor. The cytotoxin may be a native or modified cytotoxin such as Pseudomonas exotoxin (PE), Diphtheria toxin (DT), ricin, abrin, and the like.

The chimeric cytotoxin is administered to an organism containing tumor cells which are then contacted by the chimeric molecule. The targeting molecule component of the chimeric molecule specifically binds to the overexpressed IL-13 receptors on the tumor cells. Once bound to the IL-13 receptor on the cell surface, the cytotoxic effector molecule mediates internalization into the cell where the cytotoxin inhibits cellular growth or kills the cell.

The use of chimeric molecules comprising a targeting moiety joined to a cytotoxic effector molecules to target and kill tumor cells is known in the prior art. For example, chimeric fusion proteins which include interleukin 4 (IL-4) or transforming growth factor (TGFα) fused to Pseudomonas exotoxin (PE) or interleukin 2 (IL-2) fused to Diphtheria toxin (DT) have been tested for their ability to specifically target and kill cancer cells (Pastan et al., *Ann. Rev. Biochem.*, 61: 331–354 (1992)).

Although chimeric IL-4-cytotoxin molecules are known in the prior art, and IL-4 shows some sequence similarity to IL-13, it was an unexpected discovery of the present invention that cytotoxins targeted by a moiety specific to the IL-13 receptor show significantly increased efficacy as compared to IL-4 receptor directed cytotoxins. Without being bound to a particular theory, it is believed that the improved efficacy of the IL-13 chimeras of the present invention is due to at least three factors.

First, IL-13 receptors are expressed at much lower levels, if at all on non-tumor cells (e.g. monocytes, T cells, B cells). Thus cytotoxins directed to IL-13 receptors show reduced binding and subsequent killing of healthy cells and tissues as compared to other cytotoxins.

Second, the receptor component that specifically binds IL-13 appears to be expressed at significantly higher levels on solid tumors than the receptor component that binds IL-4. Thus, tumor cells bind higher levels of cytotoxic chimeric molecules directed against IL-13 receptors than cytotoxic chimeric molecules directed against IL-4 receptors.

Finally, IL-4 receptors are up-regulated when immune system cells (e.g. T-cells) are activated. This results in healthy cells, for example T-cells and B-cells, showing greater susceptibility to IL-4 receptor directed cytotoxins. Thus, the induction of an immune response (as against a cancer), results in greater susceptibility of cells of the immune system to the therapeutic agent. In contrast, IL-13 receptors have not been shown to be up-regulated in activated T cells. Thus IL-13 receptor targeted cytotoxins have no greater effect on activated T cells and thereby minimize adverse effects of the therapeutic composition on cells of the immune system.

In another embodiment, this invention also provides for compositions and methods for detecting the presence or absence of tumor cells. These methods involve providing a chimeric molecule comprising an effector molecule, that is a detectable label attached to a targeting molecule that specifically binds an IL-13 receptor. The IL-13 receptor targeting moiety specifically binds the chimeric molecule to tumor cells which are then marked by their association with the detectable label. Subsequent detection of the cell-associated label indicates the presence of a tumor cell.

In yet another embodiment, the effector molecule may be another specific binding moiety such as an antibody, a growth factor, or a ligand. The chimeric molecule will then act as a highly specific bifunctional linker. This linker may act to bind and enhance the interaction between cells or cellular components to which the fusion protein binds. Thus, for example, where the "targeting" component of the chimeric molecule comprises a polypeptide that specifically binds to an IL-13 receptor and the "effector" component is an antibody or antibody fragment (e.g. an Fv fragment of an antibody), the targeting component specifically binds cancer cells, while the effector component binds receptors (e.g., IL-2 or IL-4 receptors) on the surface of immune cells. The chimeric molecule may thus act to enhance and direct an immune response toward target cancer cells.

In still yet another embodiment the effector molecule may be a pharmacological agent (e.g. a drug) or a vehicle containing a pharmacological agent. This is particularly suitable where it is merely desired to invoke a non-lethal biological response. Thus the moiety that specifically binds to an IL-13 receptor may be conjugated to a drug such as vinblastine, doxirubicin, genistein (a tyrosine kinase inhibitor), an antisense molecule, and other pharmacological agents known to those of skill in the art, thereby specifically targeting the pharmacological agent to tumor cells over expressing IL-13 receptors.

Alternatively, the targeting molecule may be bound to a vehicle containing the therapeutic composition. Such vehicles include, but are not limited to liposomes, micelles, various synthetic beads, and the like.

One of skill in the art will appreciate that the chimeric molecules of the present invention may include multiple targeting moieties bound to a single effector or conversely, multiple effector molecules bound to a single targeting moiety. In still other embodiment, the chimeric molecules may include both multiple targeting moieties and multiple effector molecules. Thus, for example, this invention provides for "dual targeted" cytotoxic chimeric molecules in which targeting molecule that specifically binds to IL-13 is attached to a cytotoxic molecule and another molecule (e.g. an antibody, or another ligand) is attached to the other terminus of the toxin. Such a dual-targeted cytotoxin might comprise an IL-13 substituted for domain Ia at the amino terminus of a PE and anti-TAC(Fv) inserted in domain III, between amino acid 604 and 609. Other antibodies may also be suitable.

II. The Targeting Molecule.

In a preferred embodiment, the targeting molecule is a molecule that specifically binds to the IL-13 receptor. The term "specifically binds", as used herein, when referring to a protein or polypeptide, refers to a binding reaction which is determinative of the presence of the protein or polypeptide in a heterogeneous population of proteins and other biologics. Thus, under designated conditions (e.g. immunoassay conditions in the case of an antibody), the specified ligand or antibody binds to its particular "target" protein (e.g. an IL-13 receptor protein) and does not bind in a significant amount to other proteins present in the sample or to other proteins to which the ligand or antibody may come in contact in an organism.

A variety of immunoassay formats may be used to select antibodies specifically immunoreactive with an IL-13 receptor protein. For example, solid-phase ELISA immunoassays are routinely used to select monoclonal antibodies specifically imunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

Similarly, assay formats for detecting specific binding of ligands (e.g. IL-13, cpIL-13) with their respective receptors are also well known in the art. Example 1 provides a detailed protocol for assessing specific binding of labeled IL-13 by an IL-13 receptor.

The IL-13 receptor is a cell surface receptor that specifically binds IL-13 and mediates a variety of physiological responses in various cell types as described below in the description of IL-13. The IL-13 receptor may be identified by contacting a cell or other sample with labeled IL-13 and detecting the amount of specific binding of IL-13 according to methods well known to those of skill in the art. Detection of IL-13 receptors by labeled IL-13 binding is described in detail in Example 1.

Alternatively, an anti-IL-13 receptor antibody may also be used to identify IL-13 receptors. The antibody will specifically bind to the IL-13 receptor and this binding may be detected either through detection of a conjugated label or through detection of a labeled second antibody that binds the anti-IL-13 receptor antibody.

In a preferred embodiment, the moiety utilized to specifically target the IL-13 receptor is either an antibody that specifically binds the IL-13 receptor (an anti-IL-13R antibody) or a ligand, such as IL-13 or cpIL-13, that specifically binds to the receptor.

A) IL-13.

Interleukin-13 (IL-13) is a pleiotropic cytokine that is recognized to share many of the properties of IL-4. IL-13 has approximately 30% sequence identity with IL-4 and exhibits IL-4-like activities on monocytes/macrophages and human B cells (Minty et al., *Nature*, 362: 248 (1993), McKenzie et al. *Proc. Natl. Acad. Sci. USA*, 90: 3735 (1987)). In particular, IL-13 appears to be a potent regulator of inflammatory and immune responses. Like IL-4, IL-13 can up-regulate the monocyte/macrophage expression of CD23 and MHC class I and class II antigens, down-regulate the expression of Fcγ, and inhibit antibody-dependent cytotoxicity. IL-13 can also inhibit nitric oxide production as well as the expression of pro-inflammatory cytokines (e.g. IL-1, IL-6, IL-8, IL-10 and IL-12) and chemokines (MIP-1, MCP), but enhance the production of IL-1 (Minty supra.; Mckenzie et al., supra.; Zurawski et al. *Immunol. Today*, 15: 19 (1994); de Wall Malefyt et al. *J. Immunol.*, 150: 180A (1993); de Wall Malefyt et al. *J. Immunol.*, 151: 6370 (1993); Doherty et al. *J. Immunol.*, 151: 7151 (1993); and Minty et al. *Eur. cytokine Netw.*, 4: 99 (1993)).

Recombinant IL-13 is commercially available from a number of sources (see, e.g. R & D Systems, Minneapolis, Minnesota, USA, and Sanofi Bio-Industries, Inc., Tervose, Pa., USA). Alternatively, a gene or a cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, for example, Minty et al. (1993) supra. and McKenzie (1987), supra). In addition, the expression of IL-13 as a component of a chimeric molecule is detailed in Example 4.

One of skill in the art will appreciate that analogues or fragments of IL-13 bearing will also specifically bind to the IL-13 receptor. For example, conservative substitutions of residues (e.g., a serine for an alanine or an aspartic acid for a glutamic acid) comprising native IL-13 will provide IL-13 analogues that also specifically bind to the IL-13 receptor. Thus, the term "IL-13", when used in reference to a targeting molecule, also includes fragments, analogues or peptide mimetics of IL-13 that also specifically bind to the IL-13 receptor.

B) Anti-IL-13 receptor antibodies.

i) The antibodies.

One of skill will recognize that other molecules besides IL-13 will specifically bind to IL-13 receptors. Polyclonal and monoclonal antibodies directed against IL-13 receptors provide particularly suitable targeting molecules in the chimeric molecules of this invention. The term "antibody", as used herein, includes various forms of modified or altered antibodies, such as an intact immunoglobulin, various fragments such as an Fv fragment, an Fv fragment containing only the light and heavy chain variable regions, an Fv fragment linked by a disulfide bond (Brinkmann, et al. *Proc. Nati. Acad. Sci. USA*, 90: 547–551 (1993)), an Fab or (Fab)'$_2$ fragment containing the variable regions and parts of the constant regions, a single-chain antibody and the like (Bird et al., *Science* 242: 424–426 (1988); Huston et al., *Proc. Nat. Acad. Sci. USA* 85: 5879–5883 (1988)). The antibody may be of animal (especially mouse or rat) or human origin or may be chimeric (Morrison et al., *Proc Nat. Acad. Sci. USA* 81: 6851–6855 (1984)) or humanized (Jones et al., *Nature* 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual*, Cold Spring Harbor Laboratory (1988), and Asai, *Methods in Cell Biology Vol. 37: Antibodies in Cell Biology*, Academic Press, Inc. N.Y. (1993).

Antibodies that specifically bind the IL-13 receptor may be produced by a number of means well known to those of skill in the art. Generally, this involves using an antigenic component of the IL-13 receptor as an antigen to induce the production of antibodies in an organism (e.g. a sheep, mouse, rabbit, etc.). One of skill in the art will recognize that there are numerous methods of isolating all or components of the IL-13 receptor for use as an antigen. For example, IL-13 receptors may be isolated by cross-linking the receptor to a labeled IL-13 by the exposure to 2 mM disuccinimidyl suberate (DSS). Thelabeled receptor may then be isolated according to routine methods and the isolated receptor may be used as an antigen to raise anti-IL-13 receptor antibodies as described below. Cross-linking and isolation of components of the IL-13 receptor is described in Example 3.

In a preferred embodiment, however, IL-13 receptors may be isolated by means of affinity chromatography. It was a surprising discovery of the present invention that solid tumor cells overexpress IL-13 receptors. This discovery of cells overexpressing IL-13 receptor greatly simplifies the receptor isolation. Generally, approximately, 100 million renal carcinoma cells, may be solubilized in detergent with protease inhibitors according to standard methods. The resulting lysate is then run through an affinity column bearing IL-13. The receptor binds to the IL-13 in the column thereby effecting an isolation from the lysate. The column is then eluted with a low pH buffer to dissociate the IL-13 ligand from the IL-13 receptor resulting in isolated receptor. The isolated receptor may then be used as an antigen to raise anti-IL-13 receptor antibodies.

ii) Antibody production.

Methods of producing polyclonal antibodies are known to those of skill in the art. In brief, an immunogen, preferably an isolated IL-13 receptor or receptor epitope is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.).

Monoclonal antibodies may be obtained by various techniques familiar to those skilled in the art. Description of techniques for preparing such monoclonal antibodies may be found in, e.g., Stites et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256: 495–497, which discusses one method of generating monoclonal antibodies.

Summarized briefly, this method involves injecting an animal with an immunogen. The animal is then sacrificed and cells taken from its spleen, which are then fused with myeloma cells (See, Kohler and Milstein (1976) *Eur. J. Immunol.* 6: 511–519). The result is a hybrid cell or "hybridoma" that is capable of reproducing in vitro.

Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science* 246: 1275–1281. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse et al. *Science* 246: 1275–1281 (1989); and Ward, et al. *Nature* 341: 544–546 (1989). In general suitable monoclonal antibodies will usually bind their target epitope with at least a $K_D$ of about 1 mM, more usually at least about 300 $\mu$M, and most preferably at least about 0.1 $\mu$M or better.

C) Circularly permuted IL-13.

In another embodiment, the targeting moiety can be a circularly permuted IL-13 (cpIL-13). Circular permutation is functionally equivalent to taking a straight-chain molecule, fusing the ends (directly or through a linker) to form a circular molecule, and then cutting the circular molecule at a different location to form a new straight chain molecule with different termini (see, e.g., Goldenberg, et al. *J. Mol. Biol.*, 165: 407–413 (1983) and Pan et al. *Gene* 125: 111–114 (1993)). Circular permutation thus has the effect of essentially preserving the sequence and identity of the amino acids of a protein while generating new termini at different locations.

Circular permutation of IL-13 provides a means by which the native IL-13 protein may be altered to produce new carboxyl and amino termini without diminishing the specificity and binding affinity of the altered first protein relative to its native form. With new termini located away from the active (binding) site, it is possible to incorporate the circularly permuted IL-13 into a fusion protein with a reduced, or no diminution, of IL-13 binding specificity and/or avidity.

It will be appreciated that while circular permutation is described in terms of linking the two ends of a protein and then cutting the circularized protein these steps are not actually required to create the end product. A protein can be synthesized de novo with the sequence corresponding to a circular permutation of the native protein. Thus, the term "circularly permuted IL-13 (cpIL-13)" refers to all IL-13 proteins having a sequence corresponding to a circular permutation of a native IL-13 protein regardless of how they are constructed.

Generally, however, a permutation that retains or improves the binding specificity and/or avidity (as compared to the native IL-13) is preferred. If the new termini interrupt a critical region of the native protein, binding specificity and avidity may be lost. Similarly, if linking the original termini destroys IL-13 binding specificity and avidity then no circular permutation is suitable. Thus, there are two requirements for the creation of an active circularly permuted protein: 1) The termini in the native protein must be favorably located so that creation of a linkage does not destroy binding specificity and/or avidity; and 2) There must exist an "opening site" where new termini can be formed without disrupting a region critical for protein folding and desired binding activity (see, e.g., Thorton et al. *J. Mol. Biol.*, 167: 443–460 (1983)). This invention establishes that IL-13 meets these criteria and provides for circularly permuted IL-13 that having improved binding characteristics.

When circularly permuting IL-13, it is desirable to use a linker that preserves the spacing between the termini comparable to the unpermuted or native molecule. Generally linkers are either hetero- or homo-bifunctional molecules that contain two reactive sites that may each form a covalent bond with the carboxyl and the amino terminal amino acids respectively. Suitable linkers are well known to those of skill in the art and include, but are not limited to, straight or branched-chain carbon linkers, heterocyclic carbon linkers, or peptide linkers. The most common and simple example is a peptide linker that typically consists of several amino acids joined through peptide bonds to the termini of the native protein. The linkers may be joined to the terminal amino acids through their side groups (e.g., through a disulfide linkage to cysteine). However, in a preferred embodiment, the linkers will be joined to the alpha carbon amino and carboxyl groups of the terminal amino acids.

Functional groups capable of forming covalent bonds with the amino and carboxyl terminal amino acids are well known to those of skill in the art. For example, functional groups capable of binding the terminal amino group include anhydrides, carbodimides, acid chlorides, activated esters and the like. Similarly, functional groups capable of forming covalent linkages with the terminal carboxyl include amines, alcohols, and the like. In a preferred embodiment, the linker will itself be a peptide and will be joined to the protein termini by peptide bonds. A preferred linker for the circular permutation of IL-13 is Gly-Gly-Ser-Gly(SEQ ID NO:6).

In a preferred embodiment, circular permutation of IL-13 involves creating an opening such that the formation of new termini does not interrupt secondary structure crucial to the formation of a structure that specifically binds the IL-13 receptor. Even if the three-dimensional structure is compatible with joining the termini, it is conceivable that the kinetics and thermodynamics of folding would be greatly altered by circular permutation if the cleavage separates residues that participate in short range interactions that are crucial for the folding mechanism or the stability of the native state. Goldenberg, *Protein Eng.*, 7: 493–495 (1989). Thus, the choice of a cleavage site can be important to the protein's binding specificity and/or avidity.

The selection of an opening site in IL-13 may be determined by a number of factors. Preferred opening sites will be located in regions that do not show a highly regular three-dimensional structure. Thus, it is preferred that cleavage sites be selected in regions of the protein that do not show secondary structure such as alpha helices, pleated sheets, αβ barrel structures, and the like.

Methods of identifying regions of particular secondary structure of IL-13 based on amino acid sequence are widely known to those of skill in the art. See, for example, Cohen et al., *Science,* 263: 488–489 (1994). Numerous programs exist that predict protein folding based on sequence data. Some of the more widely known software packages include MatchMaker (Tripos Associates, St. Louis, Mo., USA), FASMAN from GCG (Genetics Computer Group), PHD (European Molecular Biology Laboratory, Heidelburg, Germany) and the like. In addition, the amino acid sequence of IL-13 is well known and the protein has been extensively characterized (see, e.g., WO 94/04680).

Alternatively, where the substitution of certain amino acids or the modification of the side chains of certain amino acids does not change the activity of a protein, it is expected that the modified amino acids are not critical to the protein's activity. Thus, amino acids that are either known to be susceptible to modification or are actually modified in vivo are potentially good candidates for cleavage sites.

Where the protein is a member of a family of related proteins, one may infer that the highly conserved sequences are critical for biological activity, while the variable regions are not. Preferred cleavage sites are then selected in regions of the protein that do not show highly conserved sequence identity between various members of the protein family. Alternatively, if a cleavage site is identified in a conserved region of a protein, that same region provides a good candidate for cleavage sites in a homologous protein.

Methods of determining sequence identity are well known to those of skill in the art. Sequence comparisons between two (or more) polynucleotides or polypeptides are typically performed by comparing sequences of the two sequences over a "comparison window" to identify and compare local regions of sequence similarity. Since the goal is to identify very local sequence regions that are not conserved, the comparison window will be selected to be rather small. A "comparison window", as used herein, refers to a segment of at least about 5 contiguous positions, usually about 10 to about 50, more usually about 15 to about 40 in which a sequence may be compared to a reference sequence of the same number of contiguous positions after the two sequences are optimally aligned.

Optimal alignment of sequences for comparison may be conducted by the local homology algorithm of Smith et al. *Adv. Appl. Math.* 2: 482 (1981), by the homology alignment algorithm of Needleman et al., *J. Mol. Biol.* 48:443 (1970), by the search for similarity method of Pearson et al., *Proc. Natl. Acad. Sci. USA,* 85: 2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection.

A preferred opening site in IL-13 is just prior to Met-44 of hIL-13, just at the beginning of the putative second alpha-helix resulting in a circularly permuted IL-13 having a methionine at position 44 of the native IL-13 at the amino terminus of the cpIL-13 and the Glycine at position 43 of the native IL-13 at the new carboxyl terminus of the cpIL-13. This carboxyl terminus can be joined to a second protein directly or though a spacer.

Circularly permuted IL-13 may be made by a number of means known to those of skill in the art. These include chemical synthesis, modification of existing proteins, and expression of circularly permuted proteins using recombinant DNA methodology.

The circularly permuted IL-13 may be synthesized using standard chemical peptide synthesis techniques as discussed below in section IV(B). If the linker is a peptide it may be incorporated during the synthesis. If the linker is not a peptide it may be coupled to the peptide after synthesis.

Alternatively, the circularly permuted IL-13 can be made by chemically modifying a native IL-13 (e.g. a native human IL-13). Generally, this requires reacting the IL-13 in the presence of the linker to form covalent bonds between the linker and the carboxyl and amino termini of the protein, thus forming a circular protein. New termini are then formed by cleaving the peptide bond joining amino acids at another location. This may be accomplished chemically or enzymatically using, for example, a peptidase.

If the cleavage reaction tends to hydrolyze more than one peptide bond, the reaction may be run briefly. Those molecules having more than one peptide bond cleaved will be shorter than the full length circularly permuted molecule and the latter may be isolated by any protein purification technique that selects by size (e.g., by size exclusion chromatography or electrophoresis). Alternatively, various sites in the circular protein may be protected from hydrolysis by chemical modification of the amino acid side chains which may interfere with enzyme binding, or by chemical blocking of the vulnerable groups participating in the peptide bond.

In a preferred embodiment, the circularly permuted IL-13, or fusion proteins comprising the circularly permuted IL-13 will be synthesized using recombinant DNA methodology. Generally this involves creating a DNA sequence that encodes the circularly permuted growth factor (or entire fusion protein containing the growth factor), placing the DNA in an expression cassette under the control of a particular promoter, expressing the protein in a host, isolating the expressed protein and, if required, renaturing the protein. Recombinant expression of the fusion proteins of this invention is discussed in more detail below in section IV(B).

DNA encoding circularly permuted growth factors or fusion proteins comprising circularly permuted growth factors may be prepared by any suitable method, including, for example, cloning and restriction of appropriate sequences or direct chemical synthesis by methods as discussed below. Alternatively, subsequences may be cloned and the appropriate subsequences cleaved using appropriate restriction enzymes. The fragments may then be ligated to produce the desired DNA sequence.

In a preferred embodiment, DNA encoding the circularly permuted growth factor may be produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose)

can be used as an overlapping template in a third PCR reaction. The amplified sequence will contain codons the segment on the carboxy side of the opening site (now forming the amino sequence), the linker, and the sequence on the amino side of the opening site (now forming the carboxyl sequence). The circularly permuted molecule may then be ligated into a plasmid and expressed as discussed below.

D) Modified IL-13.

One of skill in the art will appreciate that IL-13 can be modified in a variety of ways that do not destroy binding specificity and/or avidity and, in fact, may increase binding properties. Some modifications may be made to facilitate the cloning, expression, or incorporation of the circularly permuted growth factor into a fusion protein. Such modifications are well known to those of skill in the art and include, for example, a methionine added at the amino terminus to provide an initiation site, or additional amino acids placed on either terminus to create conveniently located restriction sites or termination codons.

One of skill will recognize that other modifications may be made. Thus, for example, amino acid substitutions may be made that increase specificity or binding affinity of the circularly permuted protein, etc. Alternatively, non-essential regions of the molecule may be shortened or eliminated entirely. Thus, where there are regions of the molecule that are not themselves involved in the activity of the molecule, they may be eliminated or replaced with shorter segments that merely serve to maintain the correct spatial relationships between the active components of the molecule.

E) Other targeting antibodies.

Where the chimeric molecule contains more than one targeting molecule (e.g. a dual-targeted cytotoxin), the molecule may contain targeting antibodies directed to tumor markers other than the overexpressed IL-13 receptor. A number of such antibodies are known and have even been converted to form suitable for incorporation into fusion proteins. These include anti-erbB2, B3, BR96, OVB3, anti-transferrin, Mik-β1 and PR1 (see Batra et al., *Mol. Cell. Biol.,* 11: 2200–2205 (1991); Batra et al., *Proc. Natl. Acad. Sci. USA,* 89: 5867–5871 (1992); Brinkmann, et al. *Proc. Natl. Acad. Sci. USA,* 88: 8616–8620 (1991); Brinkmann et al., *Proc. Natl. Acad. Sci. USA,* 90: 547–551 (1993); Chaudhary et al., *Proc. Natl. Acad. Sci. USA,* 87: 1066–1070 (1990); Friedman et al., *Cancer Res.* 53: 334–339 (1993); Kreitman et al., *J. Immunol.,* 149: 2810–2815 (1992); Nicholls et al., *J. Biol. Chem.,* 268: 5302–5308 (1993); and Wells, et al., *Cancer Res.,* 52: 6310–6317 (1992), respectively).

III. The Effector Molecule.

As described above, the effector molecule component of the chimeric molecules of this invention may be any molecule whose activity it is desired to deliver to cells that overexpress IL-13 receptors. Particularly preferred effector molecules include cytotoxins such as PE or DT, radionuclides, ligands such as growth factors, antibodies, detectable labels such as fluorescent or radioactive labels, and therapeutic compositions such as liposomes and various drugs.

A) Cytotoxins.

Particularly preferred cytotoxins include Pseudomonas exotoxins, Diphtheria toxins, ricin, and abrin. Pseudomonas exotoxin and Dipththeria toxin are most preferred.

i) Pseudomonas exotoxin (PE).

Pseudomonas exotoxin A (PE) is an extremely active monomeric protein (molecular weight 66 kD), secreted by *Pseudomonas aeruginosa,* which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain IA (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al., *J. Biol. Chem.* 264: 14256–14261 (1989).

Where the targeting molecule (e.g. IL-13) is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS.

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:2) (as in native PE), REDL(SEQ ID NO:3) REDL(SEQ ID NO:4), or KDEL(SEQ ID NO:5), repeats of those, or other sequences that function to maintain or recycle proteins into the endoplasmic reticulum, referred to here as "endoplasmic retention sequences". See, for example, Chaudhary et al, *Proc. Natl. Acad. Sci. USA* 87:308–312 and Seetharam et al, *J. Biol. Chem.* 266: 17376–17381 (1991).

Deletions of amino acids 365–380 of domain Ib can be made without loss of activity. Further, a substitution of methionine at amino acid position 280 in place of glycine to allow the synthesis of the protein to begin and of serine at aminoacid position 287 in place of cysteine to prevent formation of improper disulfide bonds is beneficial.

In a preferred embodiment, the targeting molecule is inserted in replacement for domain Ia. A similar insertion has been accomplished in what is known as the TGFα-PE40 molecule (also referred to as TP40) described in Heimbrook et al., *Proc. Natl. Acad. Sci., USA,* 87: 4697–4701 (1990) and in U.S. Pat. No. 5,458,878.

Preferred forms of PE contain amino acids 253–364 and 381–608, and are followed by the native sequences REDLK (SEQ ID NO:2) or the mutant sequences KDEL(SEQ ID NO:5) or RDEL(SEQ ID NO:4). Lysines at positions 590 and 606 may or may not be mutated to glutamine.

In a particularly preferred embodiment, the IL-13 receptor targeted cytotoxins of this invention comprise the PE molecule designated PE38QQR. This PE molecule is a truncated form of PE composed of amino acids 253–364 and 381–608. The lysine residues at positions 509 and 606 are replaced by glutamine and at 613 are replaced by arginine (Debinski et al. *Bioconj. Chem.,* 5: 40 (1994)).

In another particularly preferred embodiment, the IL-13 receptor targeted cytotoxins of this invention comprise the PE molecule designated PE4E. PE4E is a "full length" PE with a mutated and inactive native binding domain where amino acids 57, 246, 247, and 249 are all replaced by glutamates (see, e.g., Chaudhary et al., *J. Biol. Chem.*, 265: 16306 (1995)).

The targeting molecule (e.g. IL-13 or anti-IL-13R antibody) may also be inserted at a point within domain III of the PE molecule. Most preferably the targeting molecule is fused between about amino acid positions 607 and 609 of the PE molecule. This means that the targeting molecule is inserted after about amino acid 607 of the molecule and an appropriate carboxyl end of PE is recreated by placing amino acids about 604–613 of PE after the targeting molecule. Thus, the targeting molecule is inserted within the recombinant PE molecule after about amino acid 607 and is followed by amino acids 604–613 of domain III. The targeting molecule may also be inserted into domain Ib to replace sequences not necessary for toxicity. Debinski, et al. *Mol. Cell. Biol.*, 11: 1751–1753 (1991).

In a preferred embodiment, the PE molecules will be fused to the targeting molecule by recombinant means. The genes encoding protein chains may be cloned in cDNA or in genomic form by any cloning procedure known to those skilled in the art (see, e.g., Sambrook et al., *Molecular Cloning: A Laboratory Manual*, Cold Spring Harbor Laboratory, (1989)). Methods of cloning genes encoding PE fused to various ligands are well known to those of skill in the art (see, e.g., Siegall et al., *FASEB J.*, 3: 2647–2652 (1989); and Chaudhary et al. *Proc. Natl. Acad. Sci. USA*, 84: 4538–4542 (1987)).

Those skilled in the art will realize that additional modifications, deletions, insertions and the like may be made to the chimeric molecules of the present invention or to the nucleic acid sequences encoding IL-13 receptor-directed chimeric molecules. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

ii) Diphtheria toxin (DT).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science*, 175: 901–903 (1972); Uchida et al. *J. Biol. Chem.*, 248: 3838–3844 (1973)).

In a preferred embodiment, the targeting molecule-Diphtheria toxin fusion proteins of this invention have the native receptor-binding domain removed by truncation of the Diphtheria toxin B chain. Particularly preferred is DT388, a DT in which the carboxyl terminal sequence beginning at residue 389 is removed. Chaudhary, et al., *Bioch. Biophys. Res. Comm.*, 180: 545–551(1991).

Like the PE chimeric cytotoxins, the DT molecules may be chemically conjugated to the IL-13 receptor targeting molecule, but, in a preferred embodiment, the targeting molecule will be fused to the Diphtheria toxin by recombinant means. The genes encoding protein chains may be cloned in cDNA or in genomic form by any cloning procedure known to those skilled in the art. Methods of cloning genes encoding DT fused to various ligands are also well known to those of skill in the art (see, e.g., Wiams et al. *J. Biol. Chem.* 265: 11885–11889 (1990)).

The term "Diphtheria toxin" (DT) as used herein refers to full length native DT or to a DT that has been modified. Modifications typically include removal of the targeting domain in the B chain and, more specifically, involve truncations of the carboxyl region of the B chain.

B) Detectable labels.

Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C) Ligands.

As explained above, the effector molecule may also be a ligand or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the tumor cells overexpressing the IL-13 receptor. Suitable antibodies and growth factors are known to those of skill in the art and include, but are not limited to, IL-2, IL-4, IL-6, IL-7, tumor necrosis factor (TNF), anti-Tac, TGFα, and the like.

D) Other theraputic moieties.

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.*, 28: 341–365 (1985)

IV. Attachment of the Targeting Molecule to the Effector Molecule.

One of skill will appreciate that the targeting molecule and effector molecules may be joined together in any order. Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the chimeric molecule as a single-chain fusion protein.

A) Conjugation of the effector molecule to the targeting molecule.

In one embodiment, the targeting molecule (e.g., IL-1 3, cpIL-13, or anti-IL-13R antibody) is chemically conjugated to the effector molecule (e.g., a cytotoxin, a label, a ligand, or a drug or liposome). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine (—$NH_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Illinois.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. Cancer Res. 47: 4071–4075 (1987). In particular, production of various immunotoxins is well-known within the art and can be found, for example in "Monoclonal Antibody-Toxin Conjugates: Aiming the Magic Bullet," Thorpe et al., Monoclonal-Antibodies in Clinical Medicine, Academic Press, pp. 168–190 (1982), Waldmann, Science, 252: 1657 (1991), U.S. Pat. Nos. 4,545,985 and 4,894,443.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

B) Production of fusion proteins.

Where the targeting molecule and/or the effector molecule is relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peptide Synthesis; pp. 3–284 in The Peptides: Analysis, Synthesis, Biology. Vol. 2: Special Methods in Peptide Synthesis, Part A., Merrifield, et al. J. Am. Chem. Soc., 85: 2149–2156 (1963), and Stewart et al., Solid Phase Peptide Synthesis, 2nd ed. Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. IL-13-PE38QQR) of this invention may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention may be cloned using DNA amplification methods such as polymerase chain reaction (PCR). Thus, in a preferred embodiment, the gene for IL-13 is PCR amplified, using a sense primer containing the restriction site for NdeI and an antisense primer containing the restriction site for HindIII. In a particularly preferred embodiment, the primers are selected to amplify the nucleic acid starting at position 19, as described by McKenzie et al. (1987), supra. This produces a nucleic acid encoding the mature IL-13 sequence and having terminal restriction sites. A PE38QQR fragment may be cut out of the plasmid pWDMH4–38QQR or plasmid pSGC242FdN1 described by Debinski et al. *Int. J. Cancer,* 58: 744–748 (1994), and by Debinski et al. *Clin. Res.,* 42: 251A (abstract (1994) respectively. Ligation of the IL-13 and PE38QQR sequences and insertion into a vector produces a vector encoding IL-13 joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including *E. coli,* other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.,* Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the IL-13 receptor targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. *J. Biol. Chem.,* 268: 14065–14070 (1993); Kreitman and Pastan, *Bioconjug. Chem.,* 4: 581–585 (1993); and Buchner, et al., *Anal. Biochem.,* 205: 263–270 (1992)). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the IL-13 receptor targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

V. Identification of Target Cells.

It was a surprising discovery of the present invention that tumor cells, overexpress IL-13 receptors. In particular, carcinoma tumor cells (e.g. renal carcinoma cells) overexpress IL-13 receptors at levels ranging from about 2100 sites/cell to greater than 150,000 sites per cell. Similarly, gliomas and Kaposi's sarcoma also overexpress IL-13 receptors (IL-13R). Moreover, every cancer type tested to date appears to overexpress IL-13 receptors. Thus it appears that IL-13 receptor overexpression is general characteristic of a solid tumor neoplastic cell.

Thus, the methods of this invention can be used to target an effector molecule to virtually any neoplastic cell. Neoplasias are well known to those of skill in the art and include, but are not limited to, cancers of the skin (e.g., basal or squamous cell carcinoma, melanoma, Kaposi's sarcoma, etc.), cancers of the reproductive system (e.g., testicular, ovarian, cervical), cancers of the gastrointestinal tract (e.g., stomach, small intestine, large intestine, colorectal, etc.), cancers of the mouth and throat (e.g. esophageal, larynx, oropharynx, nasopharynx, oral, etc.), cancers of the head and neck, bone cancers, breast cancers, liver cancers, prostate cancers (e.g., prostate carcinoma), thyroid cancers, heart cancers, retinal cancers (e.g., melanoma), kidney cancers, lung cancers (e.g., mesothelioma), pancreatic cancers, brain cancers (e.g. gliomas, medulloblastomas, pituitary adeinomas, etc.) and cancers of the lymph system (e.g. lymphoma).

In a particularly preferred embodiment, the methods of this invention are used to target effector molecules to kidney cancers, colorectal cancers (especially colorectal carcinomas), to skin cancers (especially Kaposi's sarcoma), and to brain cancers (especially gliomas, and medulloblastomas).

One of skill in the art will appreciate that identification and confirmation of IL-13 overexpression by other cells requires only routine screening using well-known methods. Typically this involves providing a labeled molecule that specifically binds to the IL-13 receptor. The cells in question are then contacted with this molecule and washed. Quantification of the amount of label remaining associated with the test cell provides a measure of the amount of IL-13 receptor (IL-13R) present on the surface of that cell.

In a preferred embodiment, IL-13 receptor may be quantified by measuring the binding of $^{125}$I-labeled IL-13 ($^{125}$I-IL-13) to the cell in question. Details of such a binding assay are provided in Example 1.

VI. Pharmaceutical Compositions.

The chimeric molecules of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One preferred application is the treatment of cancer, such as by the use of an IL-13 receptor targeting molecule (e.g. IL-13 or anti-IL-13R antibody) attached to a cytotoxin.

Where the chimeric molecule comprises an IL-13 receptor targeting molecule attached to a ligand, ligand portion of the molecule is chosen according to the intended use. Proteins on the membranes of T cells that may serve as targets for the ligand includes CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte target molecules for the chimeric molecules bearing a ligand effector are described in *Leukocyte Typing III*, A. J. McMichael, ed., Oxford University Press (1987). Those skilled in the art will realize ligand effectors may be chosen that bind to receptors expressed on still other types of cells as described above, for example, membrane glycoproteins or ligand or hormone receptors such as epidermal growth factor receptor and the like.

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, is constrained by the blood-brain barrier which resists the entry of macromolecules into the subarachnoid space.

One of skill in the art will appreciate that in these instances, the therapeutic compositions of this invention can be administered directly to the tumor site. Thus, for example, brain tumors (e.g., gliomas) can be treated by administering the therapeutic composition directly to the tumor site (e.g., through a surgically implanted catheter). Where the fluid delivery through the catheter is pressurized, small molecules (e.g. the therapeutic molecules of this invention) will typically infiltrate as much as two to three centimeters beyond thetumor margin.

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

VII. Diagnostic Kits.

In another embodiment, this invention provides for kits for the treatment of tumors or for the detection of cells overexpressing IL-13 receptors. Kits will typically comprise a chimeric molecule of the present invention (e.g. IL-13-label, IL-13-cytotoxin, IL-13-ligand, etc.). In addition the kits will typically include instructional materials disclosing means of use of chimeric molecule (e.g. as a cytotoxin, for detection of tumor cells, to augment an immune response, etc.). The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

EXAMPLES

The following examples are offered to illustrate, but not to limit the claimed invention.

Example 1

Identification of Cells that Overexpress IL-13

Recombinant human IL-4 and IL-13 were labeled with $^{125}$I (Amersham Research Products, Arlington Heights, Ill., USA) by using the IODO-GEN reagent (Pierce, Rockford, Ill., USA) according to the manufacturer's instructions. The specific activity of the radiolabeled cytokines was estimated to range from 20–100 µCi/µg protein. For binding experiments, typically, 1×10$^6$ renal cell carcinoma (RCC) tumor cells were incubated at 4° C. for 2 hours with $^{125}$I-IL-13 (100 pM) with or without increasing concentrations (up to 500 nM) of unlabeled IL-13. In some experiments, IL-13R expression was examined as previously described (Obiri et al. J. Clin. Invest., 91: 88–93 (1993))). The data were analyzed with the LIGAND program (Munson et al. Anal. Biochem., 107: 220–239 (1980)) to determine receptor number and binding affinity.

Four human renal cell carcinoma (RCC) cell lines (WS-RCC, HL-RCC, PM-RCC, and MA-RCC) bound $^{125}$I-IL-13 specifically and the density of IL-13R varied from 2100 sites per cell in WS-RCC cells to 150,000 sites per cell in HL-RCC cells (Table 1). The represents an increase in IL-13 receptor expression ranging from 15 to about 500 fold as compared to normal immune cells. In contrast, IL-4 receptors overexpressed on cancers have been reported at concentrations as high as 4000 sites per cell. Scatchard analyses (Scatchard, Ann. N.Y. Acad. Sci., 51: 660–663 (1949)) revealed that only one affinity class of receptors was expressed on each cell line. The binding affinities (Kd) ranged between 100 pM to 400 pM in three RCC cell lines while HL-RCC cells expressed lower affinity receptors (Kd ~3 nM).

Although IL-13 responsiveness has previously been reported in human monocytes, B cells and pre-myeloid (TF-1) cells (see, e.g. de Waal Malefyt, et al. J. Immunol., 151: 6370–6381 (1993), de Waal Malefyt, et al. J. Immunol., 144: 629–633 (1993)), little was known about IL-13R structure or its binding characteristics in these, or any other cells. The present data show that freshly isolated human monocytes, EBV-transformed B cell line and TF-1 cell line express very few IL-13 binding sites (100–300/cell) compared to human RCC cells (Table 1). On the other hand, no binding of $^{125}$I-IL-13 was observed on H9 T cells, LAK cells and resting or PHA activated PBL. This is compatible with the fact that IL-13 responsiveness has not been observed in T lymphocytes (Punnonen et al., Proc. Natl. Acad. Sci. USA, 90: 3730–3734 (1993).

TABLE 1

Expression of IL-13 receptor by human cells.

| Cell Types | IL-13 Binding Sites/cell[a] Mean ± SD | Kd (nM) Mean ± SD |
|---|---|---|
| Renal Cell Carcinoma (RCC) | | |
| 1. WS-RCC | 2,090 ± 367 (5) | 0.247 ± 0.12 (3)[b] |
| 2. MA-RCC | 5,013 ± 1.347 (5) | 0.128 ± 0.05 (2) |
| 3. PM-RCC | 26,500 ± 5.000 (2) | 0.394 ± 0.26 (2) |
| 4. HL-RCC | 150,000 ± 15.00 (3) | 3.1 ± 0.7 (2) |
| B Lymphocytes | | |
| 1. DH (EBV-transformed B cell line) | 303 ± 90 (4) | —[d] |
| 2. RAJI (Burkitt's lymphoma) | UD[c] | — |
| Monocytes/Premyeloid cells[e] | | |
| 1. Peripheral blood monocytes | 124 | — |
| 2. U937 (premonocytic | UD | — |
| 3. TF1.J61 (premyeloid) | 130 ± 1 (2) | — |
| T Lymphocytes/LAK cells[f] | | |
| 1. PHA-activated PBL | <30 | — |
| 2. MOLT-4 (T-cell leukemia) | UD | — |
| 3. LAK cells | UD | — |

[a]IL-13 binding sites/cell were determined as described in Example 1.
[b](n) = number of experiments used to calculate mean ± standard deviation.
[c]UC = undetectable
[d]The Kd could not be reliably calculated because of low binding of $^{125}$I-IL-13
[e]The peripheral blood derived monocytes (>90% purity) were isolated by ficoll-hypaque density gradient followed by ellutriation from a leukopac obtained from normal donor.
[f]LAK cells and activated T-lymphocytes were generated by the culture of donor PBLs (106/ml) with IL-2 (500 Units/ml) for 3 days or PHA (10 µg/ml) for 3–4 days respectively.

Example 2

IL-13 and IL-4 Bind to Different Receptors

Recently, it was proposed that the IL-2R$\gamma_c$ receptor subunit is associated with IL-13R (see, e.g., Russell et al. Science 262: 1880–1883 (1993); Kondo et al. Science, 262: 1874–1877 (1993); Noguchi et al. Science, 262: 1877–1880 (1993); Kondo et al. Science 263: 1453–1454 (1994); Giri et al. EMBO J. 13: 2822–2830 (1994))) and IL-13R may share a common component with IL-4R (Zurawski et al. *EMBO J.* 12: 2663–2670 (1993); Aversa et al. *J. Exp. Med.* 178: 2213–2218 (1993)). To directly address these possibilities, radio-ligand binding experiments were performed, as described in Example 1, on HL-RCC and WS-RCC cells using $^{125}$I-IL-4 or $^{125}$I-IL-13 in the presence or absence of excess of either cytokine.

Unlabeled IL-4 more efficiently inhibited $^{125}$I-IL-4 from binding to RCC cells (84%, and 72% displacement of total binding in WS-RCC and HL-RCC, respectively) than IL-13 which also displaced $^{125}$I-IL-4 binding to these cells (61% of total binding in WS-RCC and 51% in HL-RCC) under similar conditions. On the other hand, while $^{125}$I-IL-13 binding was effectively displaced by IL-13 (about 85% of total in both cell types), it was only minimally displaced by IL-4 (12% of total displacement in WS-RCC, and 7% in HL-RCC). These results indicate that IL-4 and IL-13 both interact with each other's receptors, however, the interaction is not identical since IL-4 inhibition of $^{125}$I-IL-13 binding was weak and IL-13 inhibition of $^{125}$I-IL-4 binding was not complete. These results agree with previous observations in which IL-13 was found to compete with IL-4 binding on TF-1 cells (Zurawski et al., *EMBO J.* 12: 2663–2670 (1993)). However, in that report the converse experiment was not done. Here, the data show that even though IL-13 competed for IL-4 binding, IL-4 did not compete for IL-13 binding.

The competition by IL-13 for IL-4 binding sites on lymphoid MLA 144 cells and RAJI cell lines was also investigated. These cells were incubated with radiolabeled IL-4 with or without excess unlabeled IL-4 or IL-13. Excess unlabeled IL-4 effectively displaced labeled $^{125}$I-IL-4 bound to MLA 144 and RAJI cells, while excess IL-13 could not compete this binding. This observation is at variance to that seen with RCC cells in which IL-13 competed for IL-4 binding. The inability of IL-13 to compete for $^{125}$I-IL-4 binding to MLA 144 is consistent with the observation that IL-13 did not bind to peripheral blood T (or MLA 144) cells.

Example 3

Subunit Structure of IL-13 and IL-4 Receptors

The subunit structure of IL-13R on RCC cells was investigated by crosslinking studies. Cells (5×10$^6$) were labeled with $^{125}$I-IL-13 or $^{125}$I-IL-4 in the presence or absence of excess IL-13 or IL-4 for 2 h at 4° C. The bound ligand was cross-linked to its receptor with disuccinimidyl suberate (DSS) (Pierce, Rockford, Illinois, USA) at a final concentration of 2 mM for 30 min. Cells were lysed in a buffer containing 1% Triton X-100, 1 mM phenylmethylsulfonyl fluoride, 0.02 mM leupeptin, 5.0 μM trypsin inhibitor, 10 mM benzamidine HCl, 1 mM phenanthroline iodoacetamide, 50 mM amino caproic acid, 10 μg/ml pepstatin, and 10 μg/ml aprotinin. The cell lysates were cleared by boiling in buffer containing 2-mercaptoethanol and analyzed by electrophoresis through 8% SDS/polyacrylamide gel. The gel was subsequently dried and autoradiographed. In some experiments, the receptor/ligand complex was immunoprecipitated from the lysate overnight at 4° C. by incubating with protein A sepharose beads that had been pre-incubated with P7 anti hIL-4R or anti-$\gamma_c$ antibody and analyzed as above.

The labeled $^{125}$I-IL-13 cross-linked to one major protein on all four RCC cell lines and the complex migrated as a single broad band ranging between 68 and 80 kDa. A single band was also observed on human pre-myeloid TF-1.J61 cells only after much longer exposure of the gel. After subtracting the molecular mass of IL-13 (12 kDa), the size of IL-13 binding protein was estimated at 56 to 68 kDa. The $^{125}$I-IL-13 cross-linked band was not observed when the crosslinking was performed in the presence of 200-fold molar excess of IL-13. In addition to the major band, a faint band of approximately 45 kDa was also observed in HL-RCC and PM-RCC but not on MA-RCC cells. This band appeared to be specifically associated with IL-13R because unlabeled IL-13 competed for the binding of $^{125}$I-IL-13. This band could represent an IL-13R associated protein or a proteolytic fragment of the larger band. In contrast to the displacement of $^{125}$I-IL-13 binding by unlabeled IL-13, an excess of unlabeled IL-4 did not prevent the appearance of IL-13R band in RCC cell lines. IL-13 on the other hand competed for $^{125}$I-IL-4 binding to both major proteins on WS-RCC cells. It is of interest that $^{125}$I-IL-13-cross-linked protein was slightly larger in size in TF-1.J61, WS-RCC, PM-RCC, and HL-RCC cell lines compared to that seen in MA-RCC. Post-translational modifications, such as glycosylation or phosphorylation, may account for this difference.

Example 4

Construction of an IL-13-PE Fusion Protein

1) Construction of a Plasmid Encoding IL-13-PE38QQR

To construct the chimeric toxin a coding region of the human interleukin 13 (hIL-13) gene ( plasmid JFE14-SRα) (Minty et al., *Nature*, 362: 248 (1993), McKenzie et al. *Proc. Natl. Acad. Sci. USA,* 90: 3735 (1987)) was fused to a gene encoding PE38QQR, a mutated form of PE, thereby producing a construct (phuIL-13-Tx) encoding the chimeric molecule. Specifically, a DNA encoding human IL-13 was PCR-amplified from plasmid JFE14-SRα. New sites were introduced for the restriction endonucleases NdeI and Hind III at the 5' and 3' ends of the hIL-13 gene, respectively by PCR using a sense primer that incorporated the NdeI site and an antisense primer that incorporated the HindIII site.

The NdeI/HindIII fragment containing encoding hIL-13 was subcloned into a vector obtained by digestion of plasmid pWDMH4-38QQR (Debinski et al. *Int. J. Cancer* 58: 744–748 (1994)) or plasmid pSGC242FdN1 (Debinski et al. *Clin. Res.* 42: 251A, (abstr.) (1994) with NdeI and HindIII, to produce plasmid phuIL-13-Tx. The 5' end of the gene fusion was sequenced and showed the correct DNA of hIL-13.

Human interleukin 4 (hIL-4) was cloned into an expression vector in a similar way to hIL-13 using plasmid pWDMH4 (Debinski et al. *J. Biol. Chem.* 268: 14065–14070 (1993)) as a template for PCR amplification. Recombinant proteins were expressed in *E. coli* BL21 (lDE3) under control of the T7 late promoter (Id.). In addition to the T7 bacteriophage late promoter, the plasmids also carried a T7 transcription terminator at the end of the open reading frame of the protein, an f1 origin of replication and gene for ampicillin resistance (Debinski et al. *J. Clin. Invest.* 90: 405–411 (1992)). The plasmids were amplified in *E. coli* (HB101 or DHSα high efficiency transformation) (BRL) and DNA was extracted using Qiagen kits (Chatsworth, Calif., USA).

2) Expression and Purification of Recombinant Proteins.

*E. coli* BL21 (λDE3) cells were transformed with plasmids of interest and cultured in 1.0 liter of Super broth. Expressed recombinant human IL-13 and human IL-13-PE38QQR were localized in inclusion bodies. The recombinant proteins were isolated from the inclusion bodies as described by Debinski et al., *J. Biol. Chem.* 268: 14065–14070 (1993). After dialysis, the renatured protein of human IL-13-PE38QQR was purified on Q-Sepharose Fast Flow and by size exclusion chromatography on Sephacryl S-200HR (Pharmacia, Piscataway, N.J., USA) The initial step of hIL-13 or hIL-4 purification was conducted on SP-Sepharose Fast Flow (Pharmacia).

Protein concentration was determined by the Bradford assay (Pierce "Plus", Rockford, Ill., USA) using BSA as a standard.

Human IL-13 and IL-13-PE38QQR were expressed at high levels in bacteria as seen in SDS-PAGE analysis of the total cell extract. After initial purification on SP-Sepharose (hIL-13) or Q-Sepharose (hIL-13-PE38QQR) the renatured recombinant proteins were applied onto a Sephacryl S-200 HR Pharmacia column. Human IL-13 and hIL-13-PE38QQR appeared as single entities demonstrating the very high purity of the final products. The chimeric toxin migrated within somewhat lower than expected for 50 kda protein $M_r$ range which may be related to the hydrophobicity of the molecule. The biologic activity of the rhIL-13 was exactly the same as commercially obtained hIL-13.

Example 5

The Activity of an IL-13-PE Fusion Protein on Human Carcinoma Cells

3) Cytotoxin Activity of hIL-13-PE38QQR

The cytotoxic activity of chimeric toxins, such as hIL-13-PE38QQR, were tested by measuring inhibition of protein synthesis. Protein synthesis was assayed by plating about $1 \times 10^4$ cells per in a 24-well tissue culture plate in 1 ml of medium. arious concentrations of the chimeric toxins were added 20–28 h following cell plating.

After 20 h incubation with chimeric toxins, [$^3$H]-leucine was added to cells for 4 h, and the cell-associated radioactivity was measured. For blocking studies, rhIL-2, 4 or 13 was added to cells for 30 min before the chimeric toxin addition. Data were obtained from the average of duplicates and the assays were repeated several times.

Several established cancer cell lines were tested to determine if hIL-13-PE38QQR is cytotoxic to them. In particular, cancers derived from colon, skin and stomach were examined. The cancer cells were sensitive to hIL-13-PE38QQR with $ID_{50}$s ranging from less than 1 ng/ml to 300 ng/ml (20 pM to 6.0 nM) ($ID_{50}$ indicates the concentration of the chimeric toxin at which the protein synthesis fell by 50% when compared to the sham-treated cells). A colon adenocarcinoma cell line, Colo201, was very responsive with an $IC_{50}$ of 1 ng/ml. A431 epidermoid carcinoma cells were also very sensitive to the action of hIL-13-toxin; the $ID_{50}$ for hIL-13-PE38QQR ranged from 6 to 10 ng/ml. A gastric carcinoma CRL1739 cell line responded moderately to the hIL-13-toxin with an $ID_{50}$ of 50 ng/ml. Another colon carcinoma cell line, Colo205, had a poorer response with an $ID_{50}$ of 300 ng/ml.

The cytotoxic action of hIL-13-PE38QQR was specific as it was blocked by a 10-fold excess of hIL-13 on all cells. These data suggest that a spectrum of human cancer cells possess hIL-13 binding sites and such cells are sensitive to hIL-13-PE38QQR chimeric toxin.

Because the hIL-13R has been suggested to share the $\gamma_c$ subunit of the IL-2R (Russell et al. *Science* 262: 1880–1883 (1993)), the specificity of hIL-13-PE38QQR action on A431 and CRL1739 cells, the two cell lines with different sensitivities to the chimeric toxin was further explored. The cells were treated with hIL-13-PE38QQR with or without rhIL-2 at a concentration of 1.0 μg/ml or 10 μg/ml. The rhIL-2 did not have any blocking action on hIL-13-PE38QQR on the two cell lines, even at 10,000 fold molar excess over the chimeric toxin. These results indicate that the cell killing by the hIL-13-toxin is independent of the presence of hIL-2.

4) IL-4, Unlike IL-2, Blocks the Action of IL-13-PE38QQR

Native hIL-4 was added to cells which were then treated with hIL-13-PE38QQR. Unexpectedly, it was found that hIL-4 inhibited the cytotoxic activity of the hIL-13-toxin. This phenomenon was seen on all the tested cell lines, including Colo201, A431 and CRL1739. To investigate the possibility that hIL-13 and hIL-4 may compete for the same binding site, the cells were also treated with the hIL-4-based recombinant toxin, hIL-4-PE38QQR (Debinski et al Int. *J. Cancer* 8: 744–748 (1994)). The cytotoxic action of hIL-4-PE38QQR had already been shown to be blocked by an excess of hIL-4 but not of hIL-2 (Id.). In the present experiment hIL-13 potently blocked the cytotoxic activity of hIL-4-PE38QQR. Also, the action of another hIL-4-based chimeric toxin, hIL-4-PE4E (Debinski et al. *J. Biol. Chem.* 268: 14065–14070 (1993)), was blocked by an excess of hIL-13 on Colo201 and A431 cells. Thus, the cytotoxicity of hIL-13-PE38QQR is blocked by an excess of hIL-13 or hIL-4, and the cytotoxic action of hIL-4-PE38QQR is also blocked by the same two growth factors. However, IL-2 does not block the action of either chimeric toxin. These results strongly suggest that hIL-4 and hIL-13 have affinities for a common binding site.

This conclusion was supported by the observation of one cytokine blocking the effect of a mixture of the two chimeric toxins. When A431 cells were incubated with both hIL-3- and hIL-4-PE38QQR chimeric toxins concomitantly the cytotoxic action was preserved and additive effect was observed as expected. An excess of hIL-13 efficiently blocked the action of a mixture of the two chimeric toxins. Moreover, neither hIL-13 nor hIL-4 blocked cell killing by another mixture composed of hIL-13-PE38QQR and TGFα-PE40, a chimeric toxin which targets the EGFR (TGFα-based chimeric toxin, TGFα-PE40) (Siegall et al. *FASEB J.* 3, 2647–2652 (1992)). The same was observed on Colo201 cells.

5) Reciprocal Blocking of Chimeric Toxins by IL-13 and IL-4 is Due to Competition for Binding Sites.

The binding ability of human IL-13 was compared to human IL-4-PE38QQR in competitive binding assays. Recombinant hIL-4-PE38QQR was labeled with $^{125}$I using the lactoperoxidase method as described by Debinski et al., *J. Clin. Invest.* 90, 405–411 (1992). Binding assays were performed by a standard saturation and displacement curves analysis. A431 epidermoid carcinoma cells were seeded at $10^5$ cells per well in a 24-well tissue culture plates at 24 h before the experiment. The plates were placed on ice and cells were washed with ice-cold PBS without Ca++, Mg++ in 0.2% BSA, as described (Id.). Increasing concentrations of hIL-13 or hIL-4-PE38QQR were added to cells and incubated 30 min prior to the addition of fixed amount of $^{125}$I-hIL-4-PE38QQR (specific activity 6.2 μCi/μg protein) for 2 to 3 hours. After incubation, the cells were washed twice and lysed with 0.1 N NaOH, and the radioactivity was counted in a γ-counter.

Human IL-4-PE38QQR competed for the binding of $^{125}$I-hIL-4-PE38QQR to A431 cells with an apparent $ID_{50}$ of $4 \times 10^{-8}$ M. In addition, hIL-13 also competed for the $^{125}$I-hIL-4-PE38QQR binding site with a comparable potency to that exhibited by the chimeric protein. More extensive binding studies have shown that hIL-13 also competes for hIL-4 binding sites on human renal carcinoma cell lines.

The possibility of an influence of hIL-13 or hIL-4 on the process of receptor-mediated endocytosis and post-binding PE cellular toxicity steps was excluded by adding to cells: (i)

native PE (PE binds to the $\alpha_2$-macroglobulin receptor), (ii) TGFα-PE40, and (iii) a recombinant immunotoxin C242rF(ab')-PE38QQR (Debinski et al. *Clin. Res.* 42, 251A, (Abstr.) (1994)). C242rF(ab')-PE38QQR binds a tumor-associated antigen that is a sialylated glycoprotein (Debinski et al. *J. Clin. Invest.* 90: 405–411 (1992)). The expected cytotoxic actions of these recombinant toxins were observed and neither hIL-13 nor hIL-4 blocked these actions on A431 and Colo205 cells.

6) hIL-4 and hIL-13 Compete for a Common Binding Site on Carcinoma Cells but Evoke Different Biological Effects.

Even though hIL-13 and hIL-4 compete for a common binding site, they induce different cellular effects. Protein synthesis was inhibited in A431 epidermoid carcinoma cells in a dose-dependent manner by hIL-4 alone, or by a ADP-ribosylation deficient chimeric toxin containing hIL-4 (Debinski et al., *Int. J. Cancer* 58: 744–748 (1994)). This effect of hIL-4 or enzymatically deficient chimeric toxin can be best seen with a prolonged time of incubation (>24 h) and requires concentrations of hIL-4 many fold higher than that of the active chimeric toxin in order to cause a substantial decrease in tritium incorporation. However, when A431 cells were treated with various concentrations of hIL-13, no inhibition (or stimulation) of protein synthesis was observed, even at concentrations as high as 10 μg/ml of hIL-13 for a 72 h incubation. The same lack of response to hIL-13 was found on renal cell carcinoma cells PM-RCC. Thus, while hIL-13 and hIL-4 may possess a common binding site, they appear to transduce differently in carcinoma cells expressing this common site, such as A431 and PM-RCC cells.

Example 6

IL-13 Inhibits Growth of Human Renal Cell Carcinoma Cells Independently of the P140 IL-4 Receptor Chain Since human renal cell carcinoma cells (RCC) express a large number of intermediate to high affinity IL-13 receptors, the effect of IL-13 on in vitro growth of RCC cells was determined. The interaction between the IL-13 receptor and the IL-4 receptor was evaluated by examining the effect of anti-IL-4 and anti-IL-4R antibodies on IL-13 binding to RCC cells and the IL-13 modulation of RCC cell proliferation.

1) Inhibition of RCC Cell Growth by IL-13.

Renal cell carcinoma cells—WS-RCC and PM-RCC were derived as described previously (Obiri et al., *J. Clin. Invest.*, supra) and maintained in culture medium (CM) consisting of DMEM with 4.5 g/L glucose supplemented with 10% fetal bovine serum (FBS), glutamine (2 mM), HEPES buffer (10 mM), penicillin (100 U/ml) and streptomycin (100 μg/ml).

For proliferation assays, RCC cells were harvested, washed and resuspended in CM in which the FBS content was reduced to 0.5%. Ten thousand cells were plated in each well of a 96-well microtiter tissue culture plate and cultured overnight at 37° C. in a 5% $CO_2$ environment. IL-13 and/or IL-4 (0–1000 μg/ml) were added and incubation continued for an additional 72 h. Some cultures were concurrently treated with anti-IL-4 or anti-IL-4R antibody (1–10 μg/ml). [$^3$H]-thymidine (1 μCi/well) was added for the final 20 h of incubation. At the end of the incubation, cells were detached with trypsin or by a rapid freeze/thaw cycle and harvested unto a glass fiber filter-mat with a cell harvester (Skatron, Lier, Norway). [$^3$H]-thymidine uptake was determined with a Betaplate scintillation counter (LKB, Gaithersburg, Md.).

IL-13 inhibited cellular proliferation by up to 50% in a concentration dependent manner in WS-RCC and PM-RCC cell lines. The PM-RCC cell line was more sensitive to IL-13 since 0.1–1 ng/ml IL-13 caused a maximum inhibitory effect. The other cell line, WS-RCC required as much as 100 ng/ml of IL-13 for maximum effect. In addition, IL-13 at concentration of 10 ng/ml reduced proliferation of HL-RCC cells by 33%. Higher concentrations of IL-13 (up to 2000 ng/ml) did not have additional growth inhibitory effect. This growth inhibitory effect of IL-13 is similar to that observed with IL-4 on human RCC cells.

In order to examine the effect of IL-13 on the viability of RCC cells, the cells were cultured with IL-13 (0–100 ng/ml) at $5\times10^{-4}$/Ml in 12-well tissue culture plates. After 72 h, the cells were harvested with trypsin/versene, washed and diluted in trypan blue for cell counts. Viability was determined by trypan blue exclusion. In control cultures, the viability (mean ±SD of quadruplicate samples) was 95±10% while the viability in cultures treated with 10 or 100 ng/ml IL-13 was 92.5±9.6 and 93±8.9 respectively. Thus, IL-13 did not have direct cytotoxic effect on RCC cells.

Since IL-13 competes for IL-4 binding and a mutated form of IL-4 inhibited IL-13 and IL-4 effects (Zurawski et al., *EMBO J.*, 12: 2663 (1993))), the ability of anti-IL-4 or anti-IL-4R antibody to block both IL-4 and IL-13 growth inhibitory effects was determined. For this experiment, WS-RCC cells were treated with IL-13 or IL-4 alone, or in the presence of a neutralizing polyclonal antibody to hIL-4 or a monoclonal antibody to IL-4R (M57). This approach was chosen because a suitable anti-hIL-13 was not readily available.

[$^2$H]-thymidine uptake was significantly inhibited (p <0.05) in IL-13-treated cultures (1913±364 cpm in treated vs 3222±458 cpm in control) and in IL-4 treated cultures (2262±210 cpm in treated vs 3222±458 cpm in control). While the IL-4-mediated inhibition of proliferation was abrogated by a polyclonal anti-IL-4 antibody, the inhibitory effect of IL-13 was not affected by the addition of anti-IL-4 antibody. Furthermore, the anti-proliferative effect of IL-4 was also abrogated by M57, a monoclonal antibody against IL-4R, but the antiproliferative effect of IL-13 was not affected by this antibody.

When WS-RCC cells were treated with a combination of IL-4 and IL-13, the resulting inhibition of cellular proliferation was not significantly different from that seen in cultures treated with either cytokine alone. Thus, although IL-4 and IL-13 exert a similar effect on RCC cell growth, their actions could not be potentiated by using the two cytokines together.

2) Inhibition of RCC Colony Formation by IL-13.

To confirm the observed IL-13 mediated inhibition of RCC tumor cell proliferation, a colony formation assay was used to evaluate the effect of IL-13 on RCC cell growth. Five hundred RCC cells were plated in triplicate 100 cm$^2$ tissue culture-treated petri dishes and treated with various concentrations of IL-13. For comparative purposes, RCC cells were also similarly treated with IL-4. After a 10-day culture period, the percentages of colonies formed in control and cytokine treated groups were compared.

IL-13 inhibited colony formation in PM and WS RCC cells in a concentration dependent manner. A maximum of 34% reduction in colony formation was observed in WS-RCC cells. In repeated experiments, the maximum inhibition observed in PM-RCC cells ranged from 13–32%. The kinetics of the inhibition of colony formation in WS-RCC cells was similar to that observed in PM-RCC cells. By comparison, IL-4 inhibited colony formation in both cell lines to the same extent as did IL-13. However, PM-RCC cells appeared to be slightly more sensitive to the IL-4 effect than WS-RCC cells.

3) Effect of anti-IL-4R Antibody on IL-13 Binding.

As explained above, on human RCC cells, IL-13 compete for the binding of $^{125}$I-IL-4 but IL-4 does not compete for the binding of $^{125}$I-IL-13. In order to understand the mechanism underlying the inhibition of IL-4 binding by IL-13 and to evaluate the fidelity of ligand binding by IL-13R, the effect of anti-IL-4R antibody on 125I-IL-13 binding to PM-RCC cells, which express both IL-4R and IL-13R, was examined. As a control, the effect of this antibody on $^{125}$I-IL-4 binding to PM-RCC cells was also tested.

Recombinant human IL-4 and IL-13 were labeled with $^{125}$I (Amersham Corp.) by using the IODO-GEN reagent (Pierce Chem. Co.) according to the manufacturer's instructions. Specific activity ranged from 20 to 80 $\mu$Ci/$\mu$g for $^{125}$IL-4 and 80 to 120 $\mu$Ci/$\mu$g for $^{125}$IL-13. About 1×10$^6$ cells were incubated with radio labeled ligand (0.64 nM) in a buffered medium alone or in the presence of excess cytokine (128 nM); monoclonal (M57) or polyclonal (P2, P3, P7) rabbit antibodies raised against human IL-4R. The antibodies were used at a final dilution of 1:64. The incubation was done at 4° C. for 2 h in a shaking water bath. Cell bound radio-ligand was separated from free by centrifugation through an oil gradient and bound radioactivity determined in a gamma counter.

Both $^{125}$I-IL-13 and $^{125}$I-IL-4 specifically bound to PM-RCC cells (181,650±3,182 cpm and 9,263±576 cpm respectively). Unlabeled IL-13 competed well for $^{125}$I-IL-13 binding, however, neither IL-4 nor any of three different polyclonal antibodies to IL-4R competed for the binding of $^{125}$I-IL-13 on PM-RCC cells. Similarly, a monoclonal antibody to IL-4R (M57) did not block the binding of $^{125}$I-IL-13 to PM-RCC cells. In contrast, IL-4, IL-13 and anti-IL-4R antibody (P7) all competed for $^{125}$I-IL-4 binding on these cells.

This Example demonstrates that IL-13 inhibits the proliferation of human RCC cells in a concentration dependent manner. A maximum of 50% growth inhibition was observed and this growth inhibitory effect of IL-13 was supported by the results of a colony formation assay. It is noteworthy that the same concentration range of IL-13 inhibited colony formation in both RCC cell lines. Although a similar magnitude of growth inhibition has been reported for IL-4, this is the first report of a direct anti-tumor effect of IL-13 on RCC cells. Furthermore, inhibitory effects of IL-4 on colony formation in RCC cells have not been previously reported.

The antitumor effects of IL-13 were independent of IL-4 and did not involve IL-4R. This is evidenced by the fact that polyclonal or monoclonal antibodies to IL-4 or to the 140 kDa subunit of IL-4R had no effect on the growth inhibitory effect of IL-13. As was previously observed with IL-4, the inhibitory effect of IL-13 on RCC growth was cytostatic rather than cytotoxic since the viability in cells cultured with 10 or 100 ng/ml IL-13 was similar to that observed in control cultures after 72 h treatment.

Recently, IL-13 was shown to directly inhibit the proliferation of normal and leukemic B precursor cells in vitro by 30% (Renard et al., *Blood*, 84: 2253-(1994)). This growth inhibitory effect of IL-13 was abrogated by an antibody to the 140 kDa subunit of IL-4R. Similarly, the growth stimulatory effect of IL-13 on TF-1 cells was also shown to be blocked by an antibody to IL-4R (e.g., Tony et al., *Europ. J. Biochem.*, 225: 659 (1994)). However, in this study, none of 3 different antibodies to IL-4R blocked the growth inhibitory effect of IL-13. These contrasting findings may suggest that the antibodies used in this study and those used by others are directed at different epitopes on the IL-4R protein. An alternative explanation, which we favor, is that IL-13R on RCC are structurally different from those expressed on lymphoid cells.

Structural differences between IL-4R expressed on RCC and those expressed on lymphoid cells have been identified. These include the absence of the common gamma chain of the receptors for IL-2, 4, 7, 9, and 15 in tumor cell IL-4R, although this chain is present in IL-4R of immune cells (Obiri et al. *Oncol. Res.*, 6: 419 (1994)).

Previous studies have demonstrated that antibodies to IL-4R block cellular responsiveness to IL-13 (Tony et al., *Europ. J. Biochem.*, 225: 659 (1994)). However, the effect of these antibodies on the binding of $^{125}$I-IL-13 to the cells was not investigated. We report here that the binding of radio-labeled IL-13 to its receptors on RCC cells could not be blocked by a polyclonal antibody to IL-4R which did block the binding of radio-labeled IL-4 to its receptors. These data suggest that in RCC cells, IL-13 interaction with its receptor does not involve the 140 kDa subunit of IL-4R and IL-13 effects are probably mediated by receptors that are not shared with IL-4.

Nevertheless, results from the above described Examples do suggest some common element(s) between IL-4R and IL-13R. For example, IL-13 binds to a ~70 kDa protein and competes for IL-4 binding but IL-4 did does compete for IL-13 binding in RCC cells. In addition, IL-4 cross links to a ~70 kDa protein in addition to its primary 140 kDa binding protein. Taken together, these data suggest that the −70 kDa protein binds both IL-13 and IL-4. This indicates that the −70 kDa protein may be a homodimer in which one of the constituents binds IL-13 alone while the other binds both IL-13 and IL-4. The data further suggest that because it binds to both putative components of the ~70 kDa protein, IL-13 has a higher binding affinity to this protein than does IL-4 which appears to bind, at most, one component of the IL-13 receptor. Such an arrangement explains the finding that IL-13 competes for $^{125}$I-IL-4 binding while IL-4 does not compete for $^{125}$I-IL-13 binding on these cells. Finally, since antibody to IL-4R did not block IL-13 binding, and $^{125}$I-IL-13 cross linking to the p140 form of the IL-4R was not detected, in RCC cells, IL-13 does not appear to utilize the 140 kDa IL-4 binding subunit.

The observation that the combination of IL-4 and IL-13 does not inhibit RCC cell proliferation any better than either cytokine alone suggests that the anti-proliferative effects of IL-4 and IL-13 are mediated through a common receptor subunit or common signaling pathway. This is consistent with the notion of a shared receptor or receptor component for the two cytokines and the observation that both IL-13 and IL-4 phosphorylate a member of the Janus family of kinases (JAK 1) as well as the 140 kDa subunit of IL-4R and activate the same signal transducer and activator of transcription (STAT 6) proteins in different cell types.

In summary, IL-13, like IL-4 directly inhibits RCC proliferation in vitro. The IL-13 effect is independent of IL-4 since anti-IL-4R antibody did not inhibit IL-13 binding to its receptor and anti-IL-4R antibody did not inhibit the IL-13 effect on RCC cells. These findings suggest that IL-13R directed chimeric molecules are particularly useful for the management of RCC.

Example 7

Targeting of Interleukin-13 Receptor on Human Renal Cell Carcinoma Cells by Recombinant IL-13-Pe Cytotoxins 1) Cytotoxicity of IL-13-toxin Fusion Protein.

The cytotoxic activity of IL4-toxins was tested as described above. Typically, 10$^4$ RCC tumor cells or other cells were cultured in leucine-free medium with or without various concentrations of IL-toxin for 20–22 hours at 37° C. Then 1 µCi of [$^3$H]-Leucine (NEN Research Products, Wilmington, Del., USA) was added to each well and incubated for an additional 4 hours. Cells were harvested and radioactivity incorporated into cells was measured by a Beta plate counter (Wallac-LKB, Gaithersburg, Md., USA).

Four primary cell cultures (PM-RCC, WS-RCC, MA-RCC & HL-RCC) and 1 long term culture (RC-2) of RCC cell lines were tested because of the large number of IL-13 receptors expressed by human RCC cells (see Example 1). RCC cells were sensitive to the cytotoxic activity of IL13-toxin with IC$_{50}$ ranging from as low as 0.03 ng/ml to 350 ng/ml (<2 fM to 1 nM) (Table 2). All four primary cultures of RCC cells generated in our laboratory (18) seemed to be more sensitive to IL13-PE38QQR compared to long term RCC cell line (CAKI-1). The cytotoxic activity of IL13-toxin was specific and mediated through IL-13R, because excess IL-13 neutralized the cytotoxic activity of IL13-toxin. Thus, RCC cells are killed by IL13-PE38QQR at uniquely low concentrations of the chimeric protein.

TABLE 2

Cytotoxic activity of IL13-PE38QQR on human RCC tumor cell lines.

| Tumors | IC$_{50}$ (ng/ml)$^a$ mean + SD | IL-13 binding sites/cell | Reference No. |
| --- | --- | --- | --- |
| HL-RCC | 0.03, < 0.1 | 150,000 | 13 |
| PM-RCC | 0.090 ± 0.01 | 26,500 | 13 |
| MA-RCC | 0.340 ± .15 | 5,000 | 13 |
| WS-RCC | 17.500 ± 3.50 | 2,000 | 13 |
| CAKI-1 | 350.000$^b$ | <100 | —$^c$ |

IL13-PE38QQR (474 amino acid protein) is composed of IL-13 (114 N-terminal amino acids) and domain II and domain III of PE molecule (Debinski et al., J. Biol. Chem., 270: 16775 (1995)).
$^a$IC$_{50}$, the concentration of IL13-toxin at which 50% inhibition of protein synthesis is observed compared to untreated cells and was determined as described under "methods". The mean IC$_{50}$ for individual tumors is shown and was determined from 2–5 experiments for four RCC tumor cell lines.
$^b$Single experiment performed in quadruplicate using 5 different concentration of IL13-toxin.
$^c$current data 1) Correlation Between IL-13R Expression and Sensitivity to IL-13-toxin.

As described above, the primary RCC cell lines, such as PM-RCC, WS-RCC, HL-RCC, and MA-RCC expressed varied numbers of high- to intermediate—affinity IL-13R. However, IL-13 binding characteristics on CAKI-1 RCC cell line was not determined. IL-13 binding studies were therefore performed on these RCC cells utilizing [$^{125}$I]-IL-13.

IL-13 was iodinated with IODOGEN reagent (Pierce, Rockford, Ill., USA) according to manufacturer's instructions. The specific activity of radio-labeled IL-13 ranged between 44 to 128 µCi/µg. The IL-13 binding assay was performed by as described above (see Example 1). Briefly, RCC tumor cells were harvested after brief incubation with versene (Biowhittaker), washed three times in Hanks balanced salt solution and resuspended in binding buffer (RPMI 1640 plus 1 mM HEPES and 0.2% human serum albumin). For IL-13 displacement assay, RCC (1×10$^6$/100 µl) cells were incubated at 4° C. with $^{125}$I-IL-13 (100–200 pM) with or without increasing concentrations of unlabeled IL-13 or IL13-PE38QQR. Following a 2 h incubation, cell bound radio-ligand was separated from unbound by centrifugation through a phthalate oil gradient and radioactivity determined with a gamma counter (Wallac).

CAKI-1 RCC cell line did not bind radiolabeled IL-13 well and only expressed <100 IL-13 binding sites/cell (Table 1). The sensitivity of these cell lines to IL13-toxin also varied depending on the number of IL-13 binding sites per cell. CAKI-1 RCC cell line expressed the least number of IL-13 binding sites and were least sensitive to IL13-toxin. In contrast, HL-RCC cells were extremely sensitive and expressed 150,000 IL-13 binding sites/cell.

2) In vivo Passage of MA-RCC does not Decrease Sensitivity to IL-13-toxin.

In order to determine the antitumor activity of IL13-toxin against human RCC, human RCC cells were grown as subcutaneous tumors in nude mice, irradiated (300 rads) nude mice and in SCID mice. However, these RCC cells did not grow consistently in any of these immunoincompetent mice. In some cases tumors did grow very slowly but became centrally necrotic with a white rim of viable RCC cells.

Therefore, antitumor activity of IL13 toxin was not evaluated in vivo. However, MA-RCC were passaged in nude mice and the passaged tumors were used to prepare single cell suspensions. These cells did grow in tissue culture and after 1–3 passages, their sensitivity to IL13-toxin was determined.

MA-RCC were very sensitive to IL13-toxin and passaging of these RCC cells in vivo twice did not decrease their sensitivity. These data suggest that IL-13R levels do not change by in vivo passaging of RCC tumor cells.

3) IL13-toxin is Not Cytotoxic to Immune Cells, Monocytes, Bone Marrow-derived Cells, and Burkitt's Lymphoma Cells.

The cytotoxic activity of IL13-PE38QQR was also examined on PHA-activated T cells, a CD4+T cell lymphoma line (H9), normal bone marrow cells, EBV-transformed B cell line, 2 Burkitt's lymphoma cell lines and a premonocytic cell line (U937). As shown above in Example 1, PHA-activated T cells, H9 cells, and U937 cells did not express detectable numbers of IL-13R. Consistent with these observations, IL13-PE38QQR was not cytotoxic to any of these cell types. EBV-transformed B cell line did express about 300 IL13-binding sites/cell, however, IL13-toxin was not cytotoxic to them. Although IL-13R expression was not tested on human bone marrow cells or Burkitt's lymphoma cell lines; based on their insensitivity to IL13-toxin, it is expected that these cells also do not express IL-13R or express a low number of these receptors.

4) Clonogenic Assay.

The antitumor activity of IL13-PE38QQR was also tested by a colony-forming assay. Five hundred PM-RCC cells were plated in 100 mm petri dishes and the next day triplicate plates received IL-13 (20 ng/ml), IL13-PE38QQR (50 ng/ml) or control medium. The cells were cultured for 10 days at 37° C. in a CO$_2$ incubator. Media was then removed and colonies were fixed and stained with 0.25% crystal violet in alcohol. Colonies containing 50 or more cells were scored. The surviving fraction was calculated as the ratio of the number of colonies formed in treated and untreated cells and presented as percent survival.

Human PM-RCC cells formed colonies when 500 cells were cultured in petri dishes. Using this number of cells, PM-RCC cells formed 175 colonies with a clonogenic efficiency of 35%. When these cells were treated with IL13-PE38QQR for 10 days, only 32 colonies were formed (Table 3). However, 123 or 175 colonies were formed when cells were treated with recombinant IL-13 or media alone respectively.

TABLE 3

Effects of IL-13 and IL-13-PE38QQR on PM-RCC cells by clonogenic assay.

|  | No. Colonies ± SD | % Surviving fraction |
|---|---|---|
| PM RCC: |  |  |
| Control | 175 ± 5 | 100 |
| IL13-PE38QQR | 32 ± 4 | 18 |
| IL-13 | 123 ± 3 | 70 |
| HL RCC: |  |  |
| Control | 348 ± 9 | 100 |
| IL13-PE38QQR (5 ng/ml) | 4 ± 0.8 | 1 |
| IL13-PE38QQR (15 ng/ml) | 1 ± 1 | 0.3 |
| IL-13 | 232 ± 12 | 67 |

5) IL-4 does Not Block the Cytotoxic Activity of IL13-PE38QQR on RCC Cells.

IL-13 competed for the binding sites of IL-4 while IL-4 did not compete for the binding site of IL-13. However, in other cancer cell types IL-4 neutralized the cytotoxicity mediated by IL13-PE38QQR. The ability of IL-4 to neutralize the cytotoxicity of IL13-toxin on RCC cells was therefore tested. Only IL-13 blocked the cytotoxicity of IL13-toxin, while IL-4 did not block this cytotoxicity in all three RCC cell lines tested. 6) Binding Affinity of IL13-toxin on Human RCC Cells.

The binding affinity of IL13-PE38QQR to IL-13R was then examined. HL-RCC or PM-RCC cells were utilized for this purpose. These cells were incubated with a saturating concentration of radiolabeled IL-13 in the absence or presence of various concentrations of IL-13 or IL13-PE38QQR. In HL-RCC cells the $IC_{50}$ (the protein concentration at which 50% displacement of [$^{125}$I]-IL-13 binding is observed) for native IL-13 was ~20×10$^{-9}$ M, compared to ~180×10$^{-9}$ M with IL13-PE38QQR. Thus IL13-toxin bound to IL-13R with about 8–10 fold lower affinity compared to IL-13.

The foregoing experiments show that an IL-13 based cytotoxin, IL13-PE38QQR, is highly cytotoxic to human renal cell carcinoma cells. The $IC_{50}$ in RCC cell fines ranged from less than 0.03 ng/ml to 350 ng/ml. The cytotoxicity of the IL13-toxin was specific and mediated through IL-13R because excess IL-13 neutralized the cell killing activity of IL13-PE38QQR. These results corroborate with the data generated in a clonogenic assay that demonstrate a significant inhibition of colony formation by IL13-toxin.

Resting human cells including non-activated T cell line (H9), EBY-transformed B cell line, and promonocytic (U937) cell lines were not sensitive to the cytotoxic effect of IL13-toxin. Similarly, PHA-activated human T cells and cells obtained from normal bone marrow biopsy were also insensitive to the cytotoxic effect of IL13-PE38QQR. It has previously been reported that hematologic progenitor cell lines and fresh human bone marrow cells express low numbers of IL-4 receptors (e.g., Lowenthal et al. *J. Immunol.*, 140: 456 (1988)). However, IL-13R expression on these cells has not been determined. A recent study reported that IL-13 has a direct regulatory role in the proliferation and differentiation of primitive murine hematopoietic progenitor cells (Jacobsen et al. *J. Exp. Med.*, 180: 75 (1994)) indicating expression of some level of IL-13R on these cells. However, the example shows that IL13-toxin was not cytotoxic to fresh bone marrow derived cells indicating that progenitor cells probably express insufficient amount of IL-13R or receptors on these cells are not susceptible to the cytotoxic action of IL13-toxin.

It was shown above that IL-13 competes for the binding of IL-4 while IL-4 does not compete for the binding of IL-13 on RCC cells (Example 2). Similar to these results, the data in this example show that IL-4 does not neutralize the cytotoxic effect of EL13-PE38QQR.

It has been previously demonstrated that IL4 based cytotoxin (IL4-PE4E) is highly cytotoxic to human RCC cells. A comparison was not made between IL13-PE38QQR and IL4-PE4E because the PE portion in these two chimeric proteins is different. However, both IL-13 and IL-4 competed with the cytotoxicity of IL4-toxin. Similarly, a mutant IL-4 protein blocked the proliferative response generated by IL-4 and IL-13. These data suggest that the receptors for IL-13 and IL-4 share a component.

The data on RCC cells showed that [$^{125}$I]-IL-13 crosslinked to one major protein of ~70 kDa, which appeared to be similar in size to the smaller of the two subunits of IL-4R. The competition of IL-13 for the binding sites of IL-4, suggests that the ~70 kDa protein is shared between these two receptors. Also, IL-4 and IL-13 compete reciprocally to an internalized receptor form on some carcinoma cell lines. Recent data demonstrate that both IL-4 and IL-13 caused the phosphorylation of 140 kDa L-4 binding protein. In addition, antibody to 140 kDa IL-4 binding protein blocked the effects of IL-13 on B cells. While these studies, suggest that the 140 kDa IL-4 binding protein may be shared between these two cytokine receptors, crosslinking of [$^{125}$I]-IL-13 to the 140 kDa protein was not observed even though [$^{125}$I]-IL-4 crosslinked to this protein. These data suggest that either the 140 kDa IL-4 binding protein does not share a chain with IL-13R or the 140 kDa protein is a non-IL-13 binding component of the IL-13R system which is why IL-4 does not compete for the binding of IL-13.

It is of interest to note that IL13-toxin binds to IL-13 receptor with a lower affinity compared to that of IL-13. Since PE molecule was attached to the C-terminus of the IL-13 molecule, these data suggest that, similar to IL-4, IL-13 may interact with its receptor predominantly through C-terminal end residues. In addition, these data also suggest that a chimeric IL13 toxin molecule in which the toxin moiety is attached at a site away from the C-terminus residues should be more cytotoxic to cancer cells.

In summary, these results indicate that IL13-toxin IL13-PE38QQR is highly cytotoxic to human RCC cells which express high numbers of IL-13R. Because resting or activated immune cells or bone marrow cells are not sensitive to IL13-toxin, the data indicate that this toxin is useful for the treatment of RCC without being cytotoxic to normal immune cells.

Example 8

Human Glioma Cells Overexpress IL-13 Receptors and Are Extremely Sensitive to IL-13PE Chimeric Proteins In order to evaluate the efficacy of the chimeric immunotoxins of this invention on brain tumors, cytotoxicity (as evaluated by inhibition of protein synthesis) and competitive inhibition assays were performed on a number of brain tumor cell lines as described below.
1) Protein Synthesis Inhibition Assay.

The cytotoxic activity of chimeric toxins (e.g., hIL13-PE38QQR) was tested on brain tumor cell lines. This group of cells is represented by human gliomas and includes U-373 MG, DBTRG-05 MG, A-172, Hs 683, U-251 MG, T-98G, SNB-19, and SW-1088, and also one human neuroblastoma SK-N-MC cell line. The majority of cell lines was obtained from the ATCC and they were maintained under conditions recommended by the ATCC. The SNB-19 cell line was obtained from National Cancer Institute/Frederick Cancer Research Facility, DCT tumor repository. Both SNB-19 and SW-1088 cell lines are of neuroglial origins.

Usually about $1 \times 10^4$ cells/well were plated in a 24-well tissue culture plate in 1 ml of medium and various concentrations of chimeric immunotoxin were diluted in 0.1% bovine serum albumin (BSA)/phosphate-buffered saline (PBS) and 25 µl of each dilution was added to 1 ml of cell culture medium. After 20 hr incubation with the immunotoxins, [$^3$H]-leucine was added to the cells for 3–5 hr, and the cell-associated radioactivity was measured using a beta counter.

For blocking studies (i) recombinant hIL13 (rhIL13) or (ii) rhIL4 was added to cells for 20–30 min before the addition of chimeric toxins (CTs). Data were obtained from the average of duplicates and the assays were repeated several times.

The cancer cells were sensitive to hIL13-PE38QQR with $IC_{50}$s ranging from less than 0.1 ng/ml to more than 300 ng/ml (2 pM to 6.0 nM). (The $IC_{50}$ was calculated as the immunotoxin toxin concentration that causes 50% inhibition of tritiated leucine incorporation by the test cell line.) The cell lines fell into roughly three groups according to their responsiveness to the chimeric toxin. The first group consisting of U-373 MG, U-251 MG, SNB-19, and A-172 was killed by hIL13-PE38QQR at the lowest concentrations with $IC_{50}$s ranging from less than 0.1 to 0.5 ng/ml (2 to 10 pM). In particular, SNB-19 and A-172 had $IC_{50}$s of about 0.05 ng/ml. The second group of glioma cell lines composed of DBTRG MG and Hs-683 cells also responded very well to the hIL13-toxin with $IC_{50}$s in a range of 1–10 ng/ml (20–200 pM). The third group of glioma cell lines represented by T-98G and SW 1088 had poorer responses with $IC_{50}$s of 300 and >1000 ng/ml, respectively. The only human cancer cell line of neural origin tested, the S-K-N-MC neuroblastoma cell line, responded relatively poor to the chimeric toxin.

The cytotoxic action of hIL13-PE38QQR was specific as it was blocked by a 10- or 100-fold excess of hIL13 on the studied cells. These data indicate that most of the human glioma cancer cells examined possess hIL13 binding sites and such cells are extremely sensitive to hIL13-PE38QQR.

2) Cytotoxic Activities of Other Cytotoxin-based Chimeric Proteins in Glioma Cells.

The cytotoxic action of hIL13-PE38QQR was compared to that of chimeric toxins containing other interleukins, such as hIL4 or hIL6. It has already been shown that some glioma cell lines can be killed by hIL4-PE4E with $IC_{50}$s exceeding 10 ng/ml (Puri et al. *Int. J. Cancer*, 58: 574–581 (1994)). HIL13-PE38QQR was cytotoxic to U-251 MG, U-373 MG and DBTRG MG cell lines with $IC_{50}$s much below 10 ng/ml. The cytotoxin hILA-PE38QQR, a hIL4-based chimeric toxin resembling hIL13-PE38QQR, killed glioma cell lines, but at a concentration ranging from a factor of 10 to almost a factor of 1000 higher than that of hIL13-based toxin.

The $IC_{50}$s for hIL4-PE38QQR were higher than that seen with the hIL4-PE4E variant of the chimeric toxin (Debinski, et al. *J. Biol. Chem.*, 268: 14065–14070 (1993), Puri et al. *Int. J. Cancer*, 58: 574–581 (1994)) which is consistent with observations made with other growth factor-based chimeric proteins (Siegall et al. *Cancer Res.*, 51: 2831–2836 (1991)). Interestingly, hIL6-PE40 was also active on some human glioma cells and its activity was similar to that of the hIL4-toxin or better. However, hIL6-PE40 was still less active than the hIL13-based chimeric protein. These results show that human glioma cell lines are extremely sensitive to hIL13-PE38QQR and the cytotoxic activity of the IL13 directed cytotoxin is considerably better than that of other interleukin-based chimeric toxins.

3) Competitive Binding Assay.

The previous examples demonstrated that the action of hIL13-PE38QQR on several solid tumor cell lines is hIL13- and hIL4-specific, i.e., it can be blocked by these two cytokines but not by IL2. However, it was also observed that hILA cannot compete for hIL13 binding sites (Obiri et al. *J. Biol. Chem.*, 270: 8797–8804 (1995)) and it cannot block the cytotoxic action of the hIL13-based chimeric protein on some other cancer cell lines. Thus, the ability of hIL4 to block the IL13-toxin cytotoxin in glial cells was determined.

The hIL4 cytokine was ineffective in preventing the cytotoxicity of hIL13-PE38QQR on both U-251 MG and U-373 MG cell lines. On the other hand, hIL13 did block the cytotoxic activity of hIL4-PE38QQR. Thus, the cytotoxicity of hIL13-PE38QQR was blocked by an excess of hIL13 but not of hIL4, and the cytotoxic action of hIL4-PE38QQR was blocked by hIL13.

4) Human Glioma Cell Lines Express a Number of Receptors for IL13.

To verify that the cytotoxic activity of hIL13-PE38QQR is specific and mediated by hIL13 receptors, competitive binding assays were performed. Recombinant hIL13 was labeled with $^{125}$I (Amersham Corp.) by using the IODO-GEN reagent (Pierce) according to the manufacturer's instructions, as previously described (Obiri et al. *J. Biol. Chem.*, 270: 8797–8804 (1995)). The specific activity of the radiolabeled cytokines was estimated to range from 20 to 100 µCi/µg of protein. For binding experiments, typically $1 \times 10^6$ tumor cells were incubated at 4° C. for 2 h with $^{125}$I-hIL13 (100 pM) with or without increasing concentrations (up to 500 nM) of unlabeled cytokine. The data were analyzed with the LIGAND program (Munson, et al.,*Analy. Biochem.* 107: 220–239 (1980)) to determine receptor number and binding affinity.

Unlabeled hIL13 competed for the binding of $^{125}$I-hIL13 to U-373 MG cells efficiently. The Scatchard plot analyses of displacement experiments revealed one single binding site for hIL13 of intermediate affinity ($K_d$=1.8 nM). There were around 16,000 binding sites for hIL13 on the U-373 MG cell line. The presence of hIL13 receptors in other human glioma cell lines was also evaluated. As seen in Table 4, the glioma cells had receptors for hIL13 ranging from 500 to 30,000 molecules per cell. The hIL-13Rs expressed in human glioma cells are of intermediate affinity with $K_d$s ranging from 1 to 2 nM. It is noteworthy that four out of five cell lines studied had very

TABLE 4

Human IL-13 binding to human glioma cells.

| Cell Line | Binding Sites* molecules/cell (% CV) | Kd (nM) | hIL-13-PE38QQR $IC_{50}$ (ng/ml) |
|---|---|---|---|
| A-172 | 22,600 (15) | 1.6 | <1 |
| U-251 MG | 28,000 (12) | 2.1 | <1 |
| SNB-19 | 17,580 (19) | 1.4 | <1 |
| T-98G | 549 (37) | 1.0 | 200 |
| U-373 MG | 16,400 (14) | 1.8 | <1 |

*$1 \times 10^6$ cells were incubated with 125I-hIL-13 (100 pM) with or without increasing concentrations (up to 500 nM) of unlabeled hIL-13. Displacement curves and scatchard analyses were generated from the binding data using the LIGAND program (Munson et al., Analy. Biochem., 107: 220–239 (1980)).

high numbers of hIL-13R, i.e., above 15,000 molecules per cell. The very same cell lines were also the most responsive to the action of hIL-13-PE38QQR (Table 1). The T-98 G cell line was poorly responsive to the hIL-13-toxin[3] and was found to have only around 500 hIL-13 binding sites per cell (Table 1). Thus, specific hIL-13Rs are expressed in glioma cell lines and they mediate the cytotoxicity of hIL-13-PE38QQR.

These experiments establish that human glioma cell lines express large numbers of the receptor for the cytokine, IL13 and that it is possible to target hIL-13R with a chimeric toxin composed of the IL13 interleukin and a derivative of PE (e.g., PE38QQR). The hIL13-PE38QQR toxin is extremely active on several glioma cell lines and most of these cell lines are killed at concentrations below 1 ng/ml (<20 pM).

The action of hIL13-PE38QQR on glioma cells appears hIL13-specific because (i) hIL13 alone blocks the cytotoxicity of the chimeric toxin on all of the studied cell lines, and (ii) rhIL4 does not prevent the cytotoxic action of hIL13-PE38QQR on U-251 MG and U-373 MG glioma cells. The latter observation is different from the one made on adenocarcinomas of the skin, stomach and colon origins (Debinski et al., *J. Biol. Chem.*, 270: 16775–16780 (1995)). The action of IL13-PE38QQR was blocked efficiently by rhIL4 on these adenocarcinoma cell lines.

Receptors for IL4 and IL13 are complex and they have some common features detected in various systems, such as normal or malignant human cells. However, the U-251 MG cell line does not bind rhIL4 in a standard binding assay at 4° C. while the number of hIL13 binding sites is high on these cells. This phenomenon most probably explains why rhIL4 does not block the action of hIL13-PE38QQR on these cells. Thus, the receptors for hIL13 and hIL4 in glioma cells are different from those found in several solid tumor cell lines.

The hIL13-PE38QQR cytotoxin is considerably more active on glioma cell lines than the comparable IL4-based chimeric toxin. This difference in cytotoxicity is presumably due to the difference in numbers of IL13 and IL4 molecules that can be bound by glioma cells. Many human glioma cells bind more than 15,000 and up to 30,000 molecules of IL13 per cell while these cells bind from less than 3,000 to very few molecules of IL4 per cell. Interestingly, some human glioma cells can also be killed by a chimeric toxin containing hIL6 (Siegall et al., *Cancer Res.*, 51: 2831–2836 (1991)). However, the potency of hIL6-PE40 chimeric protein is lower from that of hIL13-PE38QQR.

Example 9

Chimeric Toxins Having Increased Cytotoxity

Two chimeric toxins were produced that had higher specific toxicities than IL-13-PE38QQR. The first cytotoxin was an IL-13-PE4E toxin where PE4E is a "full length" PE with a mutated and inactive native binding domain where amino acids 57, 246, 247, and 249 are all replaced by glutamates.

The second fusion protein was circularly permuted human IL-13 (cpIL-13) fused to PE38QQR. In particular, the circularly permuted IL-13 was produced by selecting the methionine (Met) at position 44 of human IL-13 (hIL-13), just at the beginning of the putative second alpha-helix of hIL-13, as the "new" N-terminal end of the cytokine. The "old" N-, and C-termini were connected by a short peptide having the sequence Gly-Gly-Ser-Gly(SEQ ID NO:6). The circularly permuted IL-13 (cphIL-13) was cloned in a way that the "new" C-terminus of cphIL-13 (Gly-43 in a wild-type cytokine) was fused to the N-terminal Gly of PE38QQR.

The plasmid encoding cphIL-13-PE38QQR was constructed as follows: Plasmid phIL13, encoding the 114 amino acids of hIL13 (see, e.g., Debinski et al., *J. Biol. Chem.* 270: 16775–16780 (1995)) served as a template for amplification of two separate fragments of hIL13; a fragment consisting of amino acids 1–43 and a fragment consisting of amino acids 44–114 or hIL-13 respectively. Both hIL13 1–43 and hIL13 44–114 were produced by PCR-amplification using two set of primers, primers cp1/cp2 and cp3/cp4, respectively (see Table 5, Sequence ID Nos. 1, 2, 3, and 4 respectively). Primers cp1 and cp4 introduced a new cloning site for Bam HI restriction endonuclease; primer cp2 encoded for a Hind III site and primer cp3 for Nde I restriction site. PCR-amplified cDNAs encoding for hIL13 1–43 (130 base-long) were cut with Bam HI and Hind III enzymes, and hIL13 44–114 (210 base-long) was cut with Nde I and Bam HI. These two fragments of DNA were ligated in a three-fragment ligation reaction to a vector encoding hIL13-PE38QQR (Id.) and cut with Nde I and Hind III restriction enzymes.

TABLE 5

PCR primers used to circularly permute hIL-13.

| PCR primer | Sequence | SEQ ID NO: |
|---|---|---|
| cp1 | 5'-GTGACTGCAGGTGTCCATATGTACTGTGCAGCCCTGGA-3' | 7 |
| cp2 | 5'-CCCAAACCGCGGGATCCACCGTTGAACCGTCCCTCGCGAA-3' | 8 |
| cp3 | 5'-GCAGTCGTGGGTGGATCCGGCGGTTCCCCAGGCCCTGTGCCTCC-3' | 9 |
| cp4 | 5'-TGGTGCAGCATCAAAAGCTTTGCCAGCTGTCAGGTTGATGC-3' | 10 |

The resulting plasmid, pCP/hIL13-PE38QQR, carried the cDNA for a circularly permuted hIL13 in which the new N-terminus starts at Met 44 of the wild type interleukin-13. Four additional amino acids (GlyGlySerGly)(SEQ ID NO:6) are located in between the residues 114 and I of the wild type hIL13. Circularly permuted hIL13 was linked to the first amino acid of PE38QQR. The cphIL-13-PE38QQR was expressed in *E. coli* and purified to homogeneity.

Both hIL-13-PE4E and cphIL-13-PE38QQR exhibited cytotoxic activities that were two to ten fold better than those seen with hIL-13-PE38QQR. $IC_{50}$s were as low as <0.1 ng/ml (<2 pM) on several glioma cell lines. Fresh human glioma explant cells were also killed at these low concen-

Example 10

Activity of IL-13R Directed Cytotoxins on Neutral Cancers

The cytotoxicity of two chimeric toxins (hIL-13-PE38QQR and hIL-13PE4E) was tested on cancer cell lines of neural origins. The DAOY, TE671, and D283 medulloblastoma cell lines were all responsive to hIL-13 fused to PE4E. The $IC_{50}$s recorded in an MTS colorimetric cytotoxicity assay were in a range of <1 ng/ml to 50 ng/ml (<20 pM to 1 nM, respectively). In addition, human medulloblastoma explant cells also responded well to hIL-13-PE4E.

On the other hand, the SK-N-MC and Neuro-2A neuroblastoma cells were poorly responsive ($IC_{50}$s>4 nM). The data, however, suggest that the overexpression of a receptor for hIL-13 is not restricted to gliomas, but it can be observed in neuron-derived cancers.

trations. The data suggest that the recepotr for IL-13 is an excellent target for the treatment of human gliomas using IL-13R directed cytotoxins.

Example 11

IL-13R Targeted Cytotoxins are Effective Against Kaposi's Sarcoma

The recombinant immunotoxin IL-13-PE38QQR was also tested against Kaposi's sarcoma cell lines (NCB59, KS248, KS220B, KS54A, and ARL-13). All of the cell lines were cytotoxin sensitive with $ID_{50}$s ranging from about 8 ng/ml to about 180 ng/ml. The Kaposi's sarcoma cell lines all expressed IL-13 receptors at higher levels than normal cells, however the levels were lower than the IL-13R expression levels found in renal cell carcinoma or in gliomas.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A vector comprising a nucleic acid sequence encoding a chimeric fusion protein comprising an IL-13 or circularly permuted IL-13 attached to a cytotoxic polypeptide.

2. The vector of claim 1, wherein said nucleic acid sequence encodes an IL-13-PE fusion protein.

3. The vector of claim 1, wherein said nucleic acid sequence encodes a cpIL-13-PE fusion protein.

4. The vector of claim 1, wherein said nucleic acid sequence encodes a fusion protein selected from the group consisting of IL-13-PE38QQR, cpIL-13-PE38QQR, IL-13-PE4E, and cpIL-13-PE4E.

5. The vector of claim 1, wherein the IL-13 is attached to the cytotoxic polypeptide through a linker.

6. A host cell comprising a nucleic acid sequence encoding a chimeric fusion protein comprising an IL-13 or circularly permuted IL-13 attached to a cytotoxic polypeptide.

7. The host cell of claim 6, wherein said nucleic acid sequence encodes an IL-13-PE fusion protein.

8. The host cell of claim 7, wherein said nucleic acid sequence encodes a fusion protein selected from the group consisting of IL-13-PE38QQR, cpIL-13-PE38QQR, IL-13-PE4E, and cpIL-13-PE4E.

9. The host cell of claim 6, wherein the IL-13 or the cpIL-13 is attached to the cytotoxic polypeptide through a linker.

10. The host cell of claim 6, wherein said nucleic acid sequence encodes a cpIL-13-PE fusion protein.

11. A chimeric molecule that specifically binds a tumor cell bearing an IL-13 receptor, said chimeric molecule comprising a cytotoxic molecule attached to a circularly permuted (cp) IL-13 that specifically binds an IL-13 receptor, which cpIL-13 is circularly permuted from an IL-13 having an amino terminus and a carboxy terminus, and further wherein said amino terminus and said carboxy terminus are joined through a peptide linker to form said cpIL-13.

12. A composition comprising a pharmaceutically acceptable carrier and a chimeric molecule, said chimeric molecule comprising:

an effector molecule attached to a circularly permuted ("cp") IL-13 that specifically binds to an IL-13 receptor, which cpIL-13 is circularly permuted from an IL-13 having an amino terminus and a carboxy terminus, and further wherein said amino terminus and said carboxy terminus are joined through a peptide linker to form said cpIL-13.

* * * * *

```
                          SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Gly Gly Gly Gly Ser
1               5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:
```

Arg Glu Asp Leu Lys
        1               5

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Arg Glu Asp Leu
        1

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Arg Asp Glu Leu
        1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Lys Asp Glu Leu
1

(2) INFORMATION FOR SEQ ID NO:6:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:6:

Gly Gly Ser Gly
  1

(2) INFORMATION FOR SEQ ID NO:7:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..38
      (D) OTHER INFORMATION: /note= "cp1 PCR primer"

(xi) SEQUENCE DESCRIPTION: SEQ ID NO:7:

GTGACTGCAG GTGTCCATAT GTACTGTGCA GCCCTGGA                          38

(2) INFORMATION FOR SEQ ID NO:8:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA

```
    (ix) FEATURE:
         (A) NAME/KEY: -
         (B) LOCATION: 1..40
         (D) OTHER INFORMATION: /note= "cp2 PCR primer"

(xi) SEQUENCE DESCRIPTION: SEQ ID NO:8:

CCCAAACCGC GGGATCCACC GTTGAACCGT CCCTCGCGAA                                40

(2) INFORMATION FOR SEQ ID NO:9:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..44
         (D) OTHER INFORMATION: /note= "cp3 PCR primer"

(xi) SEQUENCE DESCRIPTION: SEQ ID NO:9:

GCAGTCGTGG GTGGATCCGG CGGTTCCCCA GGCCCTGTGC CTCC                           44

(2) INFORMATION FOR SEQ ID NO:10:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..41
         (D) OTHER INFORMATION: /note= "cp4 PCR primer"

(xi) SEQUENCE DESCRIPTION: SEQ ID NO:10:

TGGTGCAGCA TCAAAAGCTT TGCCAGCTGT CAGGTTGATG C                              41
```